(12) United States Patent
Kwon et al.

(10) Patent No.: US 8,729,021 B2
(45) Date of Patent: May 20, 2014

(54) PTD-UQCRB FUSION POLYPEPTIDE, AND PHARMACEUTICAL COMPOSITION FOR PREVENTING AND TREATING ISCHEMIC DISEASES, CONTAINING SAME

(75) Inventors: Ho Jeong Kwon, Seoul (KR); Jung Hwa Chang, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 13/701,492

(22) PCT Filed: Jun. 1, 2011

(86) PCT No.: PCT/KR2011/004015
§ 371 (c)(1),
(2), (4) Date: Nov. 30, 2012

(87) PCT Pub. No.: WO2011/152662
PCT Pub. Date: Dec. 8, 2011

(65) Prior Publication Data
US 2013/0072432 A1    Mar. 21, 2013

(30) Foreign Application Priority Data
Jun. 1, 2010  (KR) .................. 10-2010-0051892

(51) Int. Cl.
| C07K 19/00 | (2006.01) |
| A61P 9/00 | (2006.01) |
| A61P 9/10 | (2006.01) |
| A61P 17/14 | (2006.01) |
| A61P 27/02 | (2006.01) |
| A61P 27/06 | (2006.01) |
| A61P 13/12 | (2006.01) |
| A61P 1/00 | (2006.01) |
| A61K 38/17 | (2006.01) |
| A61P 9/04 | (2006.01) |

(52) U.S. Cl.
USPC .................. 514/13.3; 530/350; 514/15.1

(58) Field of Classification Search
None
See application file for complete search history.

(56) References Cited

U.S. PATENT DOCUMENTS 7,902,154 B2   3/2011   Lee et al.
2005/0147971 A1*  7/2005   Lee et al. ................ 435/6

FOREIGN PATENT DOCUMENTS

| EP | 2184292 A1 | 5/2010 |
| KR | 10-2009-0033878 A | 4/2009 |
| KR | 10-2009-0121724 A | 11/2009 |

OTHER PUBLICATIONS

Ma et al. Gene Therapy. 16:320-328;2009.*
Jung et al. J Biol Chem. 285(15):11584-11595;Apr. 2010.*
Jung et al. J Biological Chem. 285(15); 11584-11595:2010.*
International Search Report for PCT/KR2011/004015.
Jung, H. et al., J BioL CHem., Epub Feb. 9, 2010, vol. 285, No. 15, pp. 11584-11595. (See abstract.)

* cited by examiner

Primary Examiner — Karlheinz R Skowronek
Assistant Examiner — Schuyler Milton
(74) Attorney, Agent, or Firm — The PL Law Group, PLLC

(57) ABSTRACT

A PTD-UQCRB fusion polypeptide, and a pharmaceutical composition for preventing and treating ischemic diseases, containing the same. The PTD-UQCRB fusion polypeptide of the present invention very effectively passes through a cell membrane to induce angiogenesis and does not cause cytotoxicity, and is thus useful for preventing and treating ischemic diseases.

4 Claims, 21 Drawing Sheets

PTD-UQCRB
(43 kDa) →

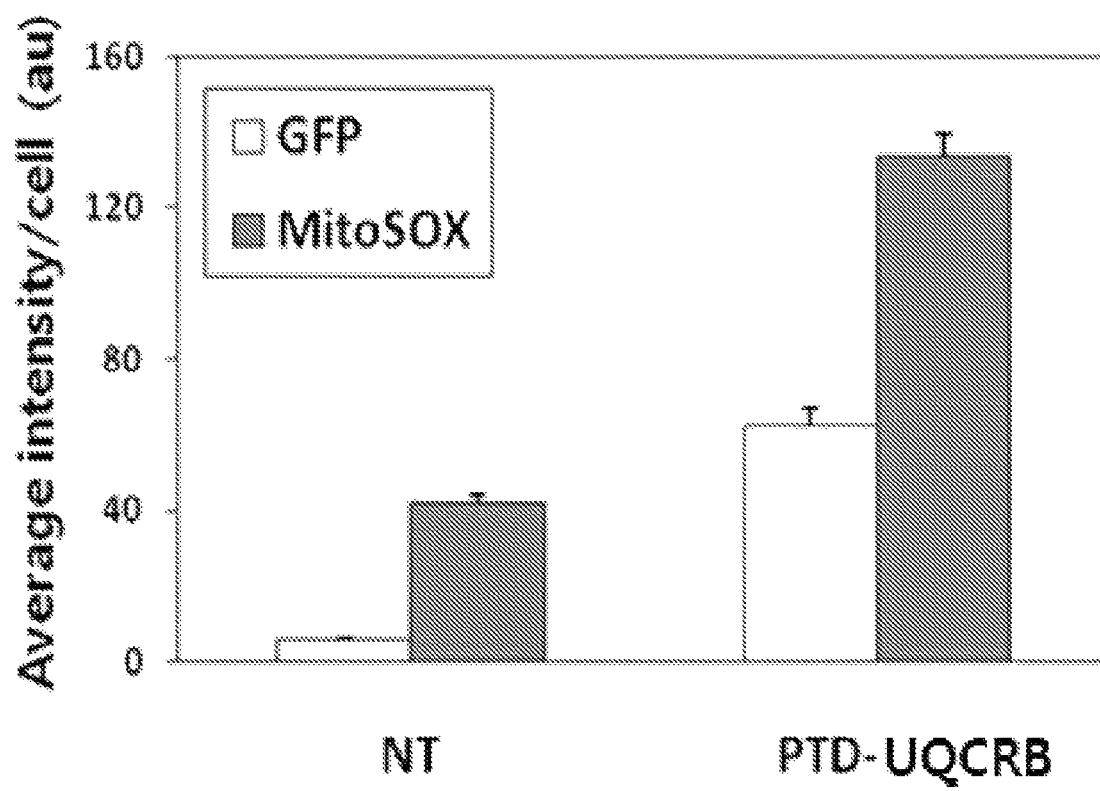

SEQUENCE LISTING

<160> NUMBER OF SEQ ID NOS: 4

<210> SEQ ID NO 1
<211> LENGTH: 111
<212> TYPE: PRT
<213> ORGANISM: Homo sapiens

<400> SEQUENCE: 1

Met Ala Gly Lys Gln Ala Val Ser Ala Ser Gly Lys Trp Leu Asp Gly
1               5                   10                  15

-continued

```
Ile Arg Lys Trp Tyr Tyr Asn Ala Ala Gly Phe Asn Lys Leu Gly Leu
            20                  25                  30

Met Arg Asp Asp Thr Ile Tyr Glu Asp Glu Asp Val Lys Glu Ala Ile
                35                  40                  45

Arg Arg Leu Pro Glu Asn Leu Tyr Asn Asp Arg Met Phe Arg Ile Lys
        50                  55                  60

Arg Ala Leu Asp Leu Asn Leu Lys His Gln Ile Leu Pro Lys Glu Gln
65                  70                  75                  80

Trp Thr Lys Tyr Glu Glu Glu Asn Phe Tyr Leu Glu Pro Tyr Leu Lys
                85                  90                  95

Glu Val Ile Arg Glu Arg Lys Glu Arg Glu Glu Trp Ala Lys Lys
                100                 105                 110

<210> SEQ ID NO 2
<211> LENGTH: 11
<212> TYPE: PRT
<213> ORGANISM: Homo sapiens

<400> SEQUENCE: 2

Tyr Ala Arg Val Arg Arg Arg Gly Pro Arg Arg
1               5                   10

<210> SEQ ID NO 3
<211> LENGTH: 333
<212> TYPE: DNA
<213> ORGANISM: Homo sapiens

<400> SEQUENCE: 3
atggctggta agcaggccgt ttcagcatca ggcaagtggc tggatggtat tcgaaaatgg      60
tattacaatg ctgcaggatt caataaactg gggttaatgc gagatgatac aatatacgag     120
gatgaagatg taaagaagc cataagaaga cttcctgaga acctttataa tgacaggatg      180
tttcgcatta agagggcact ggacctgaac ttgaagcatc agatcttgcc taaagagcag     240
tggaccaaat atgaagagga aaatttctac cttgaaccgt atctgaaaga ggttattcgg     300
gaaagaaaag aaagagaaga atgggcaaag aag                                  333

<210> SEQ ID NO 4
<211> LENGTH: 33
<212> TYPE: DNA
<213> ORGANISM: Homo sapiens

<400> SEQUENCE: 4
tatgcacgtg ttcggaggcg tggaccccgc cgc                                   33
```

PTD-UQCRB FUSION POLYPEPTIDE, AND PHARMACEUTICAL COMPOSITION FOR PREVENTING AND TREATING ISCHEMIC DISEASES, CONTAINING SAME

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2011/004015, filed on Jun. 1, 2011, which claims priority to Korean Patent Application No. 10-2010-0051892, filed Jun. 1, 2010, entire contents of which are incorporated herein by reference.

BACKGROUND

1. Field of the Invention

The present invention relates to a PTD-UQCRB fusion polypeptide, and a pharmaceutical composition for preventing and treating an ischemic disease, containing the same.

2. Description of the Related Art

Ischemia means a restriction in blood supply to tissues, causing a shortage of oxygen and glucose needed for cellular metabolism. Ischemia is generally caused by problems with blood vessels, with resultant damage to or dysfunction of tissue. It also means local anemia in a given part of a body sometimes resulting from congestion. In case of chronic ischemic heart diseases in which is one of representative ischemic diseases, myocardium is affected by abnormality of coronary circulation system and unsupplied sufficient amounts of oxygen and nutrients to accompany symptoms such as chest pain, dyspnea caused by heart failure, weakness and fainting. There has been a drastic increase in nowadays. In addition, insufficient blood supply to hair root and hair follicle prevents the formation of hair root and hair follicle such that hair loss or leukoplakia may be induced. In addition to this, blood supply interruption due to ischemia causes various ischemic diseases such as ischemic heart failure, ischemic enteritis, ischemic eye disease and ischemic limb disease. Therefore, there are attempts to treat ischemic disease by inducing angiogenesis.

VEGF (vascular Endothelial Growth Factor) is the endothelial cell-specific mitosis catalyst. VEGF is a glycoprotein with homodimer structure and exists in four different isoforms in human. VEGF-121 and 165 is a secretion protein. VEGF-189 and 206 act as growth factor by binding to heparin including proteoglycan in the cell surface or extracellular matrix. Representative receptors binding to VEGF are Flt-1 (Fml-like tyrosine kinase-1) and KDR (kinase domain-containing receptor). They are all expressed in endothelial cells, Flt-1 is mainly involved in cell migration and interaction between cells and KDR is involved in cell proliferation and survival.

Angiogenesis such as endothelial cell proliferation and migration, formation of capillaries is caused through signal transduction by binding of VEGF and its receptor and that is essential for regeneration of the wound as well as development and differentiation of organs during embryogenesis.

The fact that VEGF induce angiogenesis is well-known to those skilled in the art, and clearly supported by various literatures (Bruce I. et al, VEGF and Tumor Angiogenesis, Einstein Quart. J. Biol. and Med. 18:59-66(2001); Oettgen P, The role of ets factors in tumor angiogenesis, J Oncol., 2010: 767384. Epub 2010 May 4; Berse B. et al, Vascular permeability factor (vascular endothelial growth factor) gene is expressed differentially in normal tissues, macrophages, and tumors, Mol Biol Cell., 3(2):211-20(1992)). Therefore, the direct injection of VEGF (Vascular Endothelial Growth Factor) induces angiogenesis such that ischemic disease may be treated.

However, since administration of VEGF only cannot effectively induce all the steps of angiogenesis including disruption of basement membrane, and proliferation, migration and differentiation of epithelial cells, angiogenesis occurs less organized than the natural angiogenesis. As hypoxia is known to induce angiogenesis in nature, the regulators to hypoxia may stimulate generation of one or more angiogenic factors simultaneously, thereby being expected to induce angiogenesis in a more organized and healthier manner than induction of each individual factor.

On the other hand, ubiquinol-cytochrome c reductase binding protein (UQCRB), one of the subunits of mitochondrial Complex III, is a target protein of terpestacin which inhibits angiogenesis. Particularly, it is encoded in the nucleus[2] and plays a crucial role in the maintenance and assembly of Complex III structure[3]. Moreover, UQCRB is overexpressed in liver and stomach cancer cells and related to several diseases such as hypoglycemia, lactic acidosis, and myopathy[4].

Many reports demonstrated that the mitochondrial respiratory chain Complex III plays as a crucial modulator in hypoxia-induced angiogenesis through reactive oxygen species (ROS) production and cellular oxygen sensing[5-8]. During hypoxia, ROS generated at mitochondrial Complex III stabilize hypoxia-inducible factor 1-α (HIF-1α) protein[9], a master regulator of angiogenesis (FIG. 1). Hypoxia inducible factor (HIF) has been focused for its critical role in cell survival under hypoxic conditions and in the initiation of angiogenesis[10-11]. While HIF consist of HIF-1α and HIF-1β heterodimeric complex[12], HIF-1α protein, in particular, is responsible for initiating expression of pro-angiogenic factors such as vascular endothelial growth factor (VEGF)[13-14].

Throughout this application, several patents and publications are referenced and citations are provided in parentheses. The disclosure of these patents and publications is incorporated into this application in order to more fully describe this invention and the state of the art to which this invention pertains.

SUMMARY

The present inventors have made intensive studies to develop a pharmaceutical composition for preventing or treating an ischemic disease. As a result, the present inventors have designed a novel PTD-UQCRB (protein transduction domain-ubiquinol-cytochrome c reductase binding protein) fusion polypeptide which can transport the UQCRB into the cells and they have found out that the PTD-UQCRB fusion polypeptide effectively and safely induces angiogenesis.

Accordingly, it is an aspect of this invention to provide a PTD-UQCRB fusion polypeptide.

It is another aspect of this invention to provide an expression vector for a PTD-UQCRB fusion polypeptide.

It is still another aspect of this invention to provide a method for preparing a PTD-UQCRB fusion polypeptide.

It is further aspect of this invention to provide a pharmaceutical composition for preventing or treating an ischemic disease.

Other aspects and advantages of the present invention will become apparent from the detailed description to follow taken in conjugation with the appended claims and drawings.

In one aspect of the present invention, there is provided a PTD-UQCRB fusion polypeptide including the amino acid sequence of a PTD (protein transduction domain) and the amino acid sequence of the human UQCRB (Ubiquinol-cytochrome c reductase binding protein).

DETAILED DESCRIPTION

Figure 1:
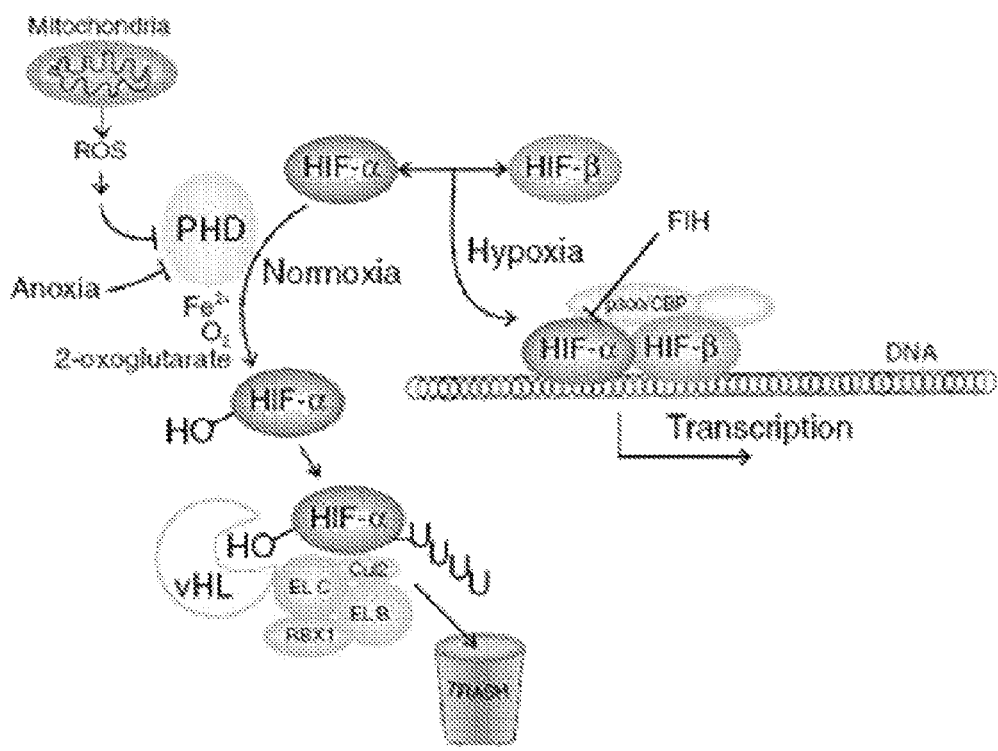
FIG. 1 schematically represents regulation of HIF in normoxia and hypoxia. This model proposes that ROS generated by the mitochondrial electron transport chain contribute to the regulation of HIF-1α stabilization during hypoxia. PHD: prolylhydroxylase, FIH: Factor inhibiting HIF, VHL: von Hippel-Lindau.

The present inventors have made intensive studies to develop a pharmaceutical composition for preventing or treating an ischemic disease. As a result, the present inventors have designed a novel PTD-UQCRB fusion polypeptide which can transport the UQCRB into the cells and they have found out that the PTD-UQCRB fusion polypeptide effectively and safely induces angiogenesis.

The fusion polypeptide of the present invention is a PTD-UQCRB fusion polypeptide including the UQCRB (Ubiquinol-cytochrome c reductase binding protein) which is fused to a PTD (protein transduction domain).

The term used herein "a PTD-UQCRB fusion polypeptide" refers to a fusion polypeptide in which the UQCRB is fused to the C-terminal or N-terminal of a PTD.

The UQCRB, one of the subunits of the PTD-UQCRB fusion polypeptide of the present invention, is a target protein of terpestacin which inhibits angiogenesis (15). Particularly, it is encoded in the nucleus and plays a crucial role in the maintenance and assembly of Complex III structure. The present inventors have found out that the intracellular UQCRB transduction induces mitochondrial ROS generation and stabilizes HIF-1α.

According to an embodiment, the human UQCRB includes the amino acid sequence as set forth in SEQ ID NO:1.

The PTD (protein transduction domain) used in fusion polypeptide of the present invention is added to influx the UQCRB into cells more effectively. By the PTD, the UQCRB of the present invention pass through the cell membrane with dendritic cell receptor-dependent manner and dendritic cell transporter-dependent manner. In other words, it is influxed by cell membrane permeability mechanism, not pinocytosis, phagocytosis and endocytosis. Therefore, the intracellular influx of the UQCRB may be achieved in more effectively manner compared with other mechanisms.

The PTD of an embodiment of the present invention is selected from the group consisting of Hph1, Tat, Penetratin, Transportan, VP-22, Amphipathic peptides, MPG, Pep-1, MAP, SAP, PPTG1, Cationic peptides, Oligoarginine, hCT (9-32), SyrB and Pvec.

According to an embodiment, the PTD is the Hph1 including the amino acid sequence as set forth in SEQ ID NO:2.

In another aspect of the present invention, there is provided an expression vector for a PTD-UQCRB fusion polypeptide including: (a) the nucleotide sequence encoding the PTD; and (b) the nucleotide sequence encoding the human UQCRB (Ubiquinol-cytochrome c reductase binding protein).

The term used herein "nucleotide" comprehensively embraces DNA (gDNA and cDNA) and RNA molecules and it may be either naturally occurring nucleotides or analogues with modification at the sugar or base (Scheit, Nucleotide Analogs, John Wiley, New York (1980); Uhlman and Peyman, Chemical Reviews, 90:543-584(1990)).

According to an embodiment, the nucleotide sequence encoding the human UQCRB includes the nucleotide sequence as set forth in SEQ ID NO:3.

In the present expression vector for the PTD-UQCRB fusion polypeptide, the nucleotide sequence encoding the human UQCRB (Ubiquinol-cytochrome c reductase binding protein) includes nucleotide sequences substantially identical to the nucleotide sequence as set forth in SEQ ID NO:3. The substantial identity means that, when a nucleotide sequence is aligned to maximally match the nucleotide sequence of the present disclosure and the alignment is analyzed using an algorithm commonly used in the art, it has an identity of at least 80%, more preferably at least 90%, and most preferably at least 95%.

According to an embodiment, the nucleotide sequence encoding the PTD includes the nucleotide sequence as set forth in SEQ ID NO:4.

To express PTD-UQCRB fusion polypeptide effectively, it is preferred that the PTD-encoding nucleotide sequence and UQCRB-encoding nucleotide sequence are contained in a suitable expression construct. In the expression construct, it is preferred that the PTD-encoding nucleotide sequence and UQCRB-encoding nucleotide sequence are operatively linked to a promoter.

The expression construct of an embodiment of the present invention may be established according to various methods known in the art. Details can be found in Sambrook et al., Molecular Cloning, A Laboratory Manual, Cold Spring Harbor Laboratory Press (2001), which is incorporated herein by reference.

Typically, the vector of an embodiment of the present disclosure may be established as an expression vector. In addition, the vector of the present disclosure may be established using a prokaryotic cell as a host.

When the vector of an embodiment of the present disclosure is an expression vector and a prokaryotic cell is a host, a powerful promoter for transcription (e.g., tac promoter, lac promoter, lacUV5 promoter, lpp promoter, $p_L^\lambda$ promoter, $p_R^\lambda$ promoter, rac5 promoter, amp promoter, recA promoter, SP6 promoter, trp promoter, T7 promoter, etc.), a ribosome binding site for initiation of translation, and a transcription/translation termination sequence are included in general. When *E. coli* is used as the host cell, the promoter and operator regions involved in tryptophan biosynthesis in *E. coli* (Yanofsky, C., *J. Bacteriol.*, 158: 1018-1024 (1984)) and the left side promoter of phage λ ($p_L^\lambda$ promoter, Herskowitz, I. and Hagen, D., *Ann. Rev. Genet.*, 14: 399-445 (1980)) can be used as a regulatory site.

Meanwhile, the vector that can be used in the present disclosure can be constructed by using a plasmid (e.g., pSC101, ColE1, pBR322, pUC8/9, pHC79, pUC19, pET, etc.), a phage (e.g., λgt4λB, λ-Charon, λΔz1, M13, etc.) or a virus (e.g., SV40, etc.) that are typically used in the art.

The vector of an embodiment of the present disclosure may be fused with other sequence, if necessary, for easier purification of the IFN-α fused protein of the present disclosure expressed thereby. The fused sequence may be, for example, glutathione S-transferase (Pharmacia, USA), maltose-binding protein (NEB, USA), FLAG (IBI, USA), hexahistidine (6xHis; Qiagen, USA), or the like, but is not limited thereto.

According to an embodiment, the fused protein expressed by the vector of an embodiment of the present disclosure is purified by affinity chromatography, for example, HisPur cobalt resin affinity chromatography or Ni-affinity column.

Meanwhile, the expression vector of an embodiment of the present disclosure may include an antibiotic-resistant gene typically used in the art as a selection marker. Examples thereof include but are not limited to genes resistant to ampicillin, gentamycin, carbenicillin, chloramphenicol, streptomycin, kanamycin, geneticin, neomycin and tetracycline.

In still another aspect of the present invention, there is provided a method for preparing a PTD-UQCRB fusion polypeptide, including: (a) transforming a host cell with the expression vector for a PTD-UQCRB fusion polypeptide; and (b) obtaining the PTD-UQCRB fusion polypeptide by culturing the transformed host cell.

With respect to a host cell, any one known in the art to be capable of stably and continuously cloning and expressing the vector of the present disclosure can be used. Examples thereof include *Bacillus* sp. strains including *E. coli* JM109, *E. coli* BL21(DE3), *E. coli* RR1, *E. coli* LE392, *E. coli* B, *E. coli* X 1776, *E. coli* W3110, *Bacillus subtilis, Bacillus thuringiensis*, etc., and intestinal bacteria and strains including *Salmonella typhimurium, Serratia marcescens* and various *Pseudomonas* sp, preferably starpLys S *E. coli*.

Delivery of the vector of the present disclosure into the host cell can be carried out by the $CaCl_2$ method (Cohen, S. N. et al., *Proc. Natl. Acac. Sci. USA*, 9: 2110-2114 (1973)), the Hannahan's method (Cohen, S. N. et al., *Proc. Natl. Acac. Sci. USA*, 9: 2110-2114 (1973); Hanahan, D., *J. Mol. Biol.*, 166: 557-580 (1983)), the electroporation method (Dower, W. J. et al., *Nucleic. Acids Res.*, 16: 6127-6145 (1988)), and the like.

The vector introduced into the host cell may be expressed there. In this case, a large amount of the fused protein of the present disclosure can be produced.

In further aspect of the present invention, there is provided a pharmaceutical composition for preventing or treating an ischemic disease including: (a) a pharmaceutically effective amount of a PTD-UQCRB fusion polypeptide; and (b) a pharmaceutically acceptable carrier.

According to an embodiment, the PTD-UQCRB fusion polypeptide includes the amino acid sequence as set forth in SEQ ID NO:1 and the amino acid sequence as set forth in SEQ ID NO:2.

When PTD-UQCRB fusion protein permeates into the cells, the mitochondrial Complex III-derived ROS generation is induced. Mitochondrial ROS inhibits PHD, the HIF hydroxylase, to stabilize HIF-1α. Stable HIF-1α can dimerize with HIF-1β and the heterodimer complex translocates into the nucleus to bind on HRE promoter. Consequently, the target gene such as VEGF can be transcribed and lead to angiogenesis. As results of experiments, these results demonstrated that the PTD-UQCRB fusion protein of the present invention induce the expression of the VEGF and lead to angiogenesis under normoxic conditions.

According to an embodiment, the ischemic disease is selected from the group consisting of ischemic heart disease, ischemic myocardial infarction, ischemic heart failure, ischemic enteritis, ischemic vascular disease, ischemic eye disease, ischemic retinopathy, ischemic glaucoma, ischemic renal failure, ischemic bald disease, ischemic stroke and ischemic limb disease.

The term as used herein "pharmaceutically effective amount" refers to an amount sufficient to achieve efficacies and activities for treating an ischemic disease.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995).

The pharmaceutical composition according to the present invention may be administered parenterally. For parenteral administration, it may be administered intravenously, subcutaneously, intramusculerly, intraperitoneally, transdermally or intra-articularly.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-100 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further include a dispersion agent or a stabilizer.

The features and advantages of one or more embodiments of the present invention will be summarized as follows:

(i) Embodiments of the present invention provide a PTD-UQCRB fusion polypeptide, and a pharmaceutical composition for preventing and treating ischemic diseases containing the same.

(ii) The PTD-UQCRB fusion polypeptide of one or more embodiments of the present invention very effectively passes through a cell membrane to induce angiogenesis without causing cytotoxicity. Therefore, it is useful for preventing and treating ischemic diseases.

EXAMPLES OF THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

1. Molecular Cloning, Expression and Purification of PTD-UQCRB Fusion Protein

To obtain the PTD-UQCRB fusion protein from bacteria, a PCR-amplified full-length cDNA of UQCRB (accession no. NM_006294) was inserted into the EcoRI/XhoI site of cell permeable protein transduction domain (Hph1 domain) containing pRSET-B expression vector which was kindly provided by Prof. Sang Kyou Lee, Yonsei University.

BL21 (DE3) starpLysS *E. coli* strains transformed with plasmids encoding the PTD-UQCRB fusion protein were grown in Luria-Bertani (LB) medium containing ampicillin (50 µg/mL) and chloramphenicol (34 µg/mL) at 37° C. up to an absorbance of 0.6 at 600 nm. The protein expression was induced with 0.1 M isopropyl-β-D-thiogalactopyranoside (IPTG) and cells were grown for additional 16 h. The cells were collected by centrifugation, suspended in lysis buffer (50 mM $NaH_2PO_4$, 300 mM NaCl, 10 mM imidazole, protease inhibitor cocktail tablets, pH 8.0), and then disrupted by sonication. Following centrifugation at 13,000 rpm, 4° C. for 15 min, Ni-NTA agarose beads (Qiagen, Hilden, Germany) were added to the supernatant and incubated at 4° C. for 2 h. After incubation with beads, supernatant was loaded on Polyprep columns (Bio-Rad, Hercules, Calif., USA). Bound proteins were washed with wash buffer (50 mM $NaH_2PO_4$, 300 mM NaCl, 20 mM imidazole, pH 8.0) and eluted with elution buffer (50 mM $NaH_2PO_4$, 300 mM NaCl, 250 mM imidazole, pH 8.0). The eluted proteins were desalted using PD-10 Sephadex G-25 (GE Healthcare, Buckinghamshire, UK), supplemented with 10% glycerol, separated into aliquots and flash-frozen at −20° C.

2. Cell Culture

HeLa cells were cultured with Dulbecco's modified eagle medium (DMEM, Gibco-BRL, Grand Island, N.Y., USA) supplemented with 10% fetal bovine serum (FBS, Gibco-BRL, Grand Island, N.Y., USA). Human umbilical vein endothelial cells (HUVECs) were seeded in gelatin coated plates with endothelial cell basal medium (EBM-2, Cambrex Walkersville, Md., USA) supplemented with 10% FBS. HepG2 cells were cultured with Roswell Park Memorial Institute medium (RPMI) 1640 (RPMI, Gibco-BRL, Grand Island, N.Y., USA) supplemented with 10% FBS. HT1080 cells were cultured with Minimum essential medium (MEM, Gibco-BRL, Grand Island, N.Y., USA) supplemented with 10% FBS. The cells were maintained in a humidified incubator supplemented with 5% $CO_2$.

3. Fluorescence Imaging

To monitor the localization of PTD-UQCRB, HeLa cells were incubated with 4 μM of PTD-UQCRB for 1 h and then cells were fixed with 4% formaldehyde (Sigma, St. Louis, Mo.). After wash with PBS, cells were co-stained with 1 μg/mL Hoechst solution and 0.5 μg/mL Mitotracker solution for 30 min. Finally cells were washed with distilled water, mounted and analyzed by confocal microscopy (Carl Zeiss LSM 510 META, Germany).

4. Cell Growth Assay

HUVECs were grown in EBM-2 supplemented with 10% FBS at 37° C. in a humidified atmosphere of 5% $CO_2$. HeLa cells were grown in DMEM supplement with 10% FBS at the same condition of HUVECs. The growth of cells were measured using a 3-(4,5-dimethylthiazol-2-yl)-2,5-diphenyltetrazolium bromide (MTT) assay. The cells ($3 \times 10^3$ cells/well) were inoculated in 96-well culture plates and incubated for 24 h for stabilization. Various concentrations of PTD-UQCRB were added to each well and incubated for 2 days and performed MTT assay. 50 μL of MTT (2 mg/mL stock solution, Sigma) was added and the plate was incubated for an additional 4 h. After removal of medium, 100 μL of DMSO was added. The plate was read at 540 nm by universal microplate reader (Bio-Tek Instruments, Inc., Winooski, Vt., USA).

5. Measurement of Mitochondrial ROS

Mitochondrial ROS level was measured using the red mitochondrial superoxide indicator, MitoSOX™ (Gibco-BRL, Grand Island, N.Y., USA). HeLa cells were grown on the microscope cover glasses (Decklaser, Lauda-Konlgshofen, Germany) and treated with 1 μM of MitoSOX™. Following incubation for 20 min at 37° C., cells were washed with PBS and then treated with PTD-UQCRB and incubated again for 2 h at 37° C. After wash with PBS, samples were stained with 1 μg/mL Hoechst solution to visualize the nucleus. Cells were washed with PBS and then fixed with 4% formaldehyde for 15 min at 37° C. After 3 times wash with PBS, samples were finally washed with distilled water and mounted and analyzed by fluorescence microscopy (Olympus America, Inc., Melville, N.Y., USA).

6. SDS-PAGE and Western Blot Analysis

HeLa cells grown in 6-well plates were lysed and the lysates were separated by 10% SDS-PAGE, followed by transferred to PVDF membranes (Millipore, Bedford, Mass.) using standard electroblotting procedures. Blots were blocked and immunolabeled overnight at 4° C. with primary antibodies, including anti-HIF-1a (BD, Bedford, Mass., USA), anti-VEGF (Santa Cruz, Santa Cruz, Calif., USA,), and anti-tubulin (Upstate, Lake Placid, N.Y.) antibodies. Immunolabeling was detected by an enhanced chemiluminescence (ECL) kit (GE Healthcare, Buckinghamshire, UK) according to the manufacturer's instructions.

7. HRE Reporter Gene Assay

HepG2 cells were grown at 37° C. and 5% $CO_2$ in DMEM supplemented with 10% FBS. The cells were seeded in 6-well plates 24 h before transfection of plasmids with transfection reagent Lipofectamine LTX (Invitrogen, NY, USA) according to the manufacturer's instructions. Normoxic condition is set with 5% $CO_2$ while the hypoxic treatment was performed in an $N_2$—O—$CO_2$ incubator with 2% $O_2$ and 5% $CO_2$ at 37° C. for 4 h. Reporter plasmid construct for a luciferase reporter assay (HRE-luciferase) was kindly provided by Dr. Futoshi Shibasaki (Tokyo Metropolitan Institute of Medical Science, Japan) and have been described previously. HepG2 cells were transfected with 0.5 μg reporter construct and after incubation of 24 h, cells were collected and lysed with lysis buffer (50 mM Tris, 150 mM NaCl, 10% glycerol, 0.5% Triton X-100, pH 8.0) and centrifuged. Cell lysates were obtained and assayed for luciferase activity using SteadyGlo® Luciferase Assay System (Promega, Madison, Wis., USA). Activity was read with FL600 Microplate Fluorescence Reader (Bio-Tek Instrument, Inc., Winooski, Vt., USA).

8. Invasion Assay

The invasiveness of HUVECs was examined in vitro using a Transwell chamber system with 8.0-μm pore-sized polycarbonate filter inserts (Corning Costar, Cambridge, Mass.). The lower side of the filter was coated with 10 μL of gelatin (1 mg/mL, Sigma, Mo., USA), whereas the upper side was coated with 10 μL of Matrigel (3 mg/mL, BD, Bedford, Mass., USA). The HUVECs ($1 \times 10^5$ cells) were placed in upper part of the filter and conditioned medium (CM) was applied to the lower part. The chamber was then incubated at 37° C. for 16 h and then fixed with methanol and stained with hematoxylin and eosin (Sigma, Mo., USA). The invaded cells on the lower part of the filter were detected using optical microscopy at ×100 magnification.

9. Wound Formation and Treatment

The back skin of 5 week-old mouse (BALB/c nude female, Orient Bio, Korea) was removed in the shape of rectangle with the width of $1.5 \times 1.5$ $cm^2$ to get wounds.

The mouse was intraperitoneally administrated with tribromoethanol (Avertin®, 250 mg/kg) to anesthetize and subcutaneously injected with Ketoprofen (0.1 mg/kg) to relieve pain as analgesic. After surgery, the analgesic was administered to alleviate pain for 4 days at intervals of 24 hours. Mice were divided into three (3) groups, PTD-UQCRB, PTD-EGFP and PBS (n=7). 200 μg of PTD tagged fusion protein or PBS was mixed with fibrin matrix (Greenplast, Greencross PD Co., Korea) and topically administered to the wound portion in each group. After protein treatment, the mice were wrapped with Tegaderm (3M Health Care, USA) as dressing on the wound. All research protocol was approved by the Yonsei University Laboratory Animal Research Center.

10. Histological or Immunohistochemical Analysis

On 2 weeks after the surgery, mouse was euthanized to obtain the tissue of the regenerated portion. The tissue was subjected to histological or immunohistochemical analysis. The sample was fixed in 4% paraformaldehyde solution and prepared into paraffin. The paraffin block was sliced to 4-μm thickness. The slides were stained with hematoxylin-eosin (H-E), Masson's trichrome (M-T). In addition, the slides were incubated with antibodies for anti-involucrin (Abcam, Cambridge, UK) and anti-α-actin (Abcam) as primary antibody and stained using diaminobenzidine (DAB substrate kit, Vector laboratories, USA).

11. Measurement of Epidermal Thickness

The epidermal thickness was verified using measuring the thickness of three points of wound in staining images of H-E, M-T and involucrin as epidermal marker. Quantitative analysis of the results was expressed as the mean±SD.

Result

Figures 2A, 2B:
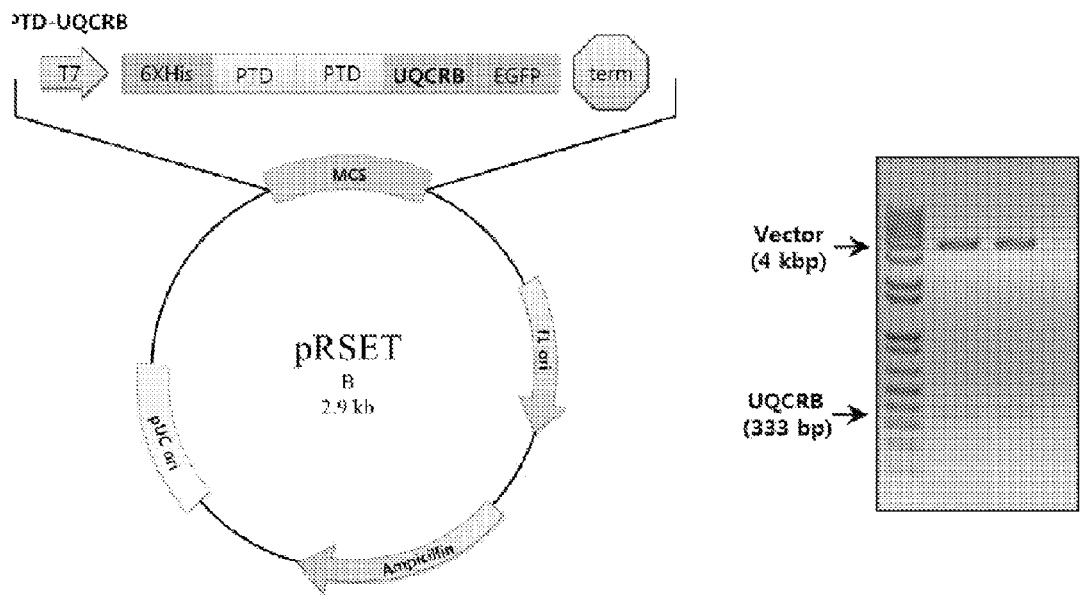
FIG. 2 schematically represents gene cloning of PTD-UQCRB fusion protein. (A) Left: DNA construct of PTD-UQCRB, Right: DNA gel electrophoresis image after restriction enzyme cutting. (B) Sequence of subcloned DNA construct. Purple: PTD sequences, Blue: Restriction enzyme sites (first: GAATTC for EcoRI, second: CTCGAG for XhoI), Red: full length of UQCRB gene.

1. Generation of PTD-UQCRB Fusion Protein 1.1 Gene Cloning of PTD-UQCRB DNA Construct To explore the biological function of terpestacin-binding mitochondrial protein (UQCRB), a DNA construct which can express the cell permeable UQCRB was designed (FIG. 2A). Full length of UQCRB gene was subcloned into the pRSET-B protein expression vector which contained protein transduction domain (PTD). This protein transduction domain encodes cell permeable peptide (Hph1) which enables to deliver its fusion partner into the cells. A 6x His tag was inserted to use for protein purification with Ni-NTA. Enhanced green fluorescence protein (EGFP) was also included to detect the intracellular delivery of PTD-UQCRB fusion protein.

In order to confirm that the PTD-UQCRB DNA construct was set properly, it was cut with restriction enzymes, EcoRI and XhoI. Following DNA gel electrophoresis showed that UQCRB was correctly inserted in the PTD-containing vector according to its restriction enzyme sites (FIG. 2A). Moreover, PTD-UQCRB DNA construct was sequenced and the sequencing results also showed that PTD and UQCRB were perfectly inserted (FIG. 2B).

1.2 Expression and Purification of PTD-UQCRB Fusion Protein

Figure 3A:
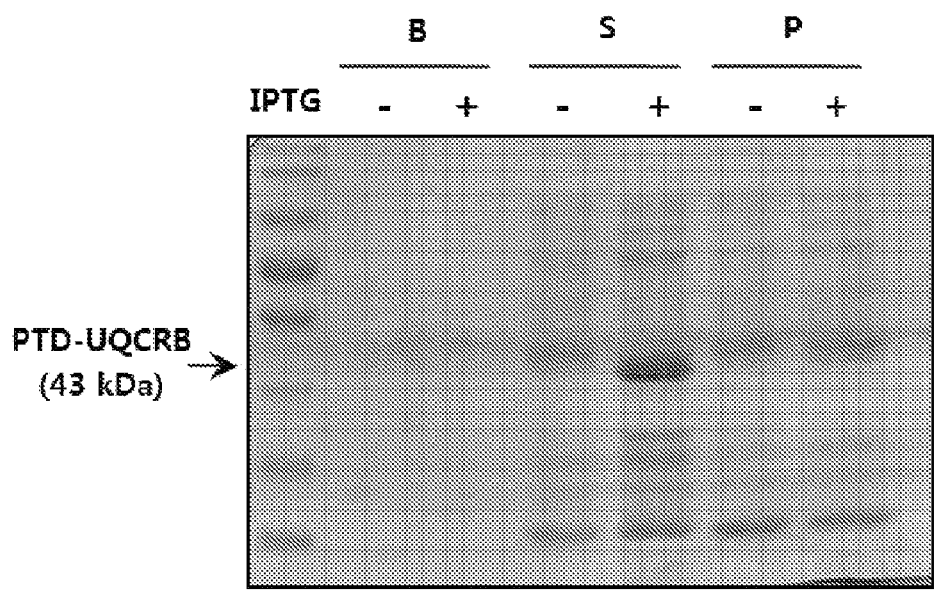
FIG. 3 represents expression and purification of PTD-UQCRB fusion proteins. (A) Series of PTD-UQCRB fusion proteins are expressed on BL21 cell line (B: BL21, S: BL21 starpLysS, P: BL21 pLysS). Molecular weights of the PTD-UQCRB fusion proteins are 43 kDa. (B) Cultured BL21 starpLysS expressing green fluorescence with IPTG induction. (C) Ni-NTA agarose beads bind with expressed PTD-UQCRB fusion proteins which are tagged with EGFP after IPTG induction. (D) Purified PTD-UQCRB fusion proteins (43 kDa).
Figure 3B:
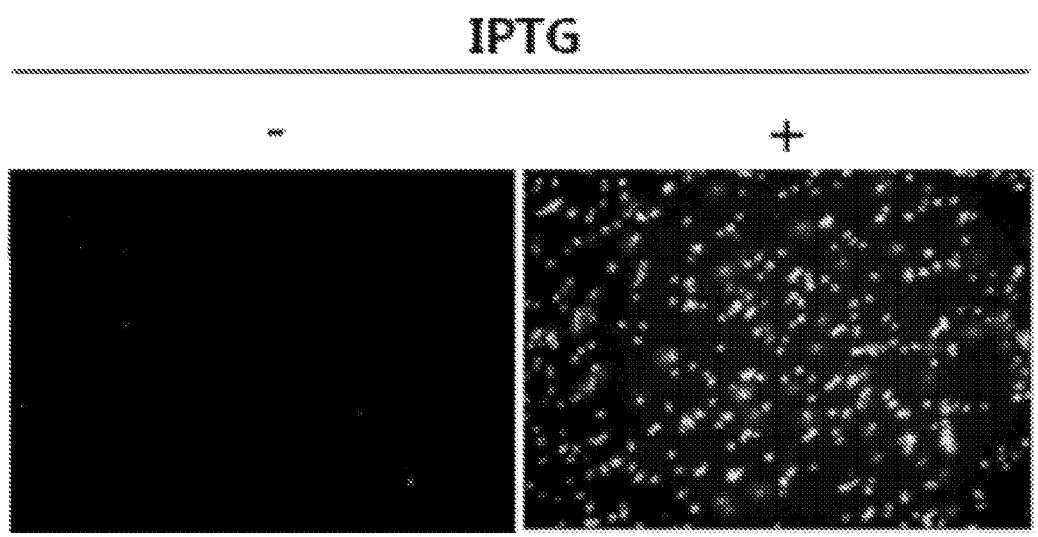
Figure 3C:
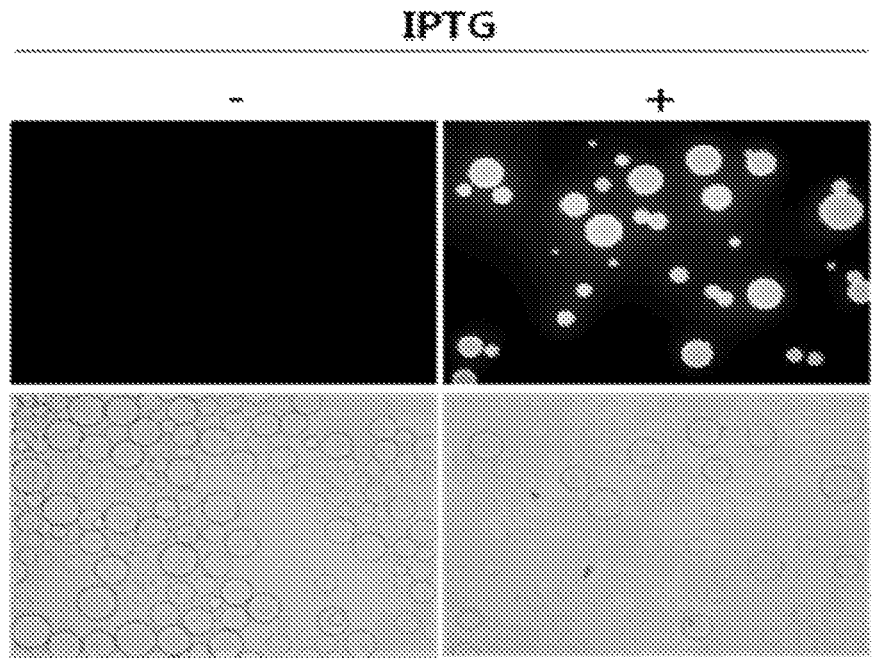
Figure 3D:
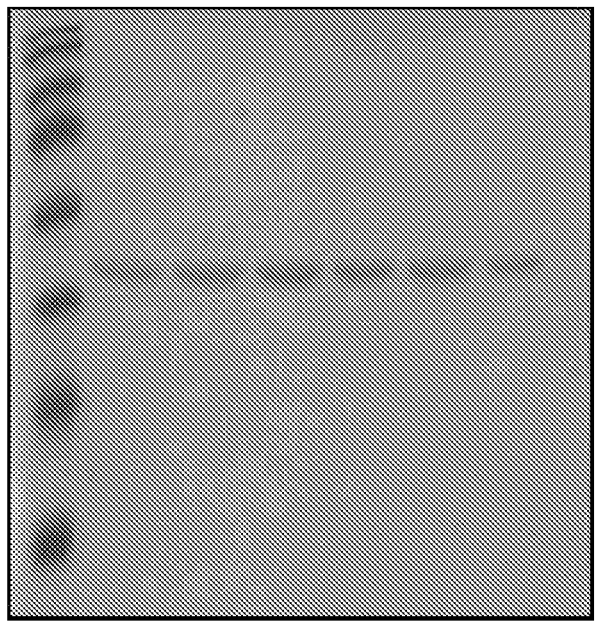

To obtain the PTD-UQCRB fusion protein, six bacteria strains for protein expression were tested. Out of six strains, BL21 starpLysS strain was chosen (FIG. 3A) because of its excellent capability for PTD-UQCRB fusion protein expression as compared with the other strains. However, PTD-UQCRB fusion proteins were fastidious to set the expression condition probably due to UQCRB's hydrophobic properties. Despite the difficulties in expression of PTD-UQCRB fusion proteins, they were well induced with IPTG in BL21 starpLysS in a soluble form at the low temperature, 18° C. After induction with IPTG, the cultured E. coli shows green fluorescence due to the expressed proteins tagged with EGFP (FIG. 3B). Besides, green fluorescence was also detected on the Ni-NTA agarose beads after supernatants of cell lysates were incubated with the beads for 2 h (FIG. 3C). PTD-UQCRB fusion proteins were purified after a series of standard purification steps using imidazole containing buffers and followed by desalting step. Imidazole was subsequently removed via desalting and purified PTD-UQCRB fusion proteins were identified by SDS-PAGE (FIG. 3D).

2. Intracellular Delivery of PTD-UQCRB Fusion Protein

Figure 4A:
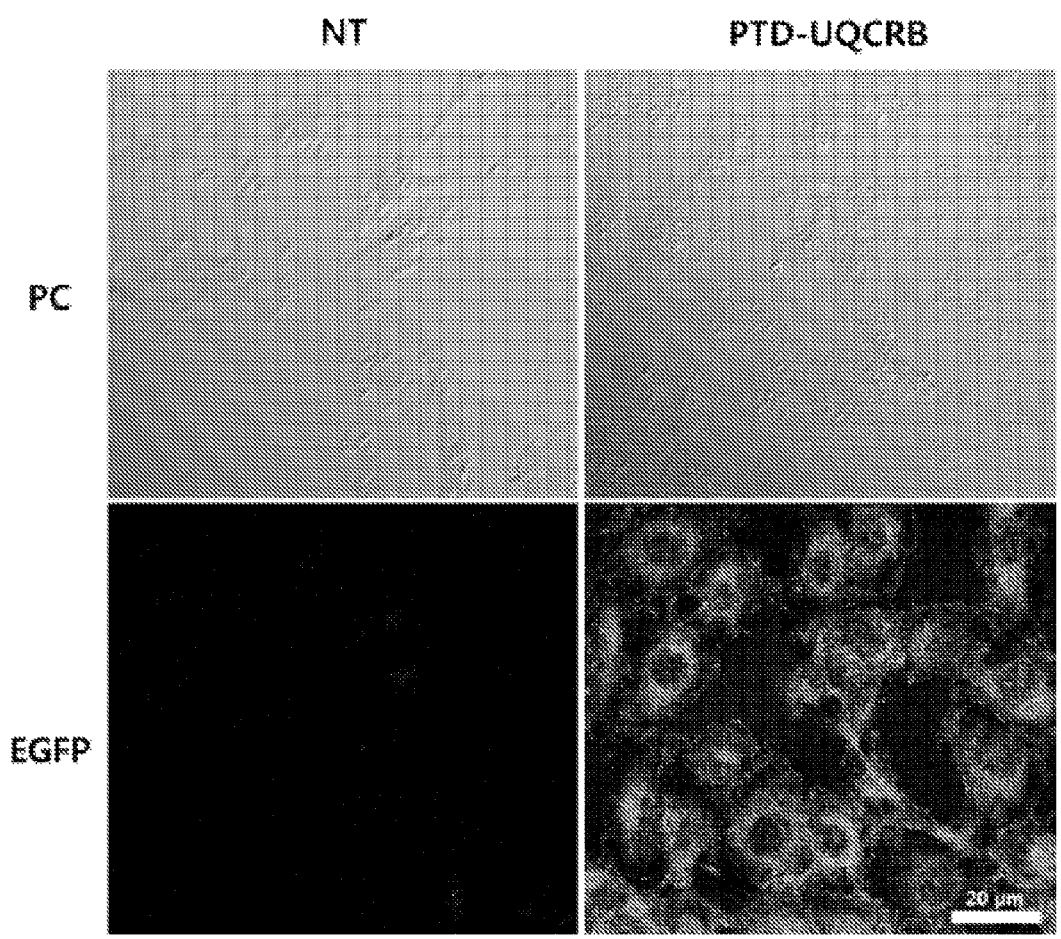
FIG. 4 represents subcellular localization of PTD-UQCRB fusion protein. (A) After 0.5 µM of PTD-UQCRB fusion proteins were transduced into HT1080 cells for 1 h, PTD-UQCRB contained supernatants were removed. The cells were fixed immediately and the localization of PTD-UQCRB fusion proteins was detected by confocal microscopy (NT: non-treated, PC: phase contrast). Scale bar, 20 µm. (B) After 2 µM of PTD-UQCRB fusion proteins were transduced into HT1080 cells for 1 h, PTD-UQCRB contained supernatants were removed. The cells were fixed and stained with Hoechst and Mirotracker to observe the localization of PTD-UQCRB fusion proteins by confocal microscopy (NT: non-treated). Scale bar, 20 µm.
Figure 4B:
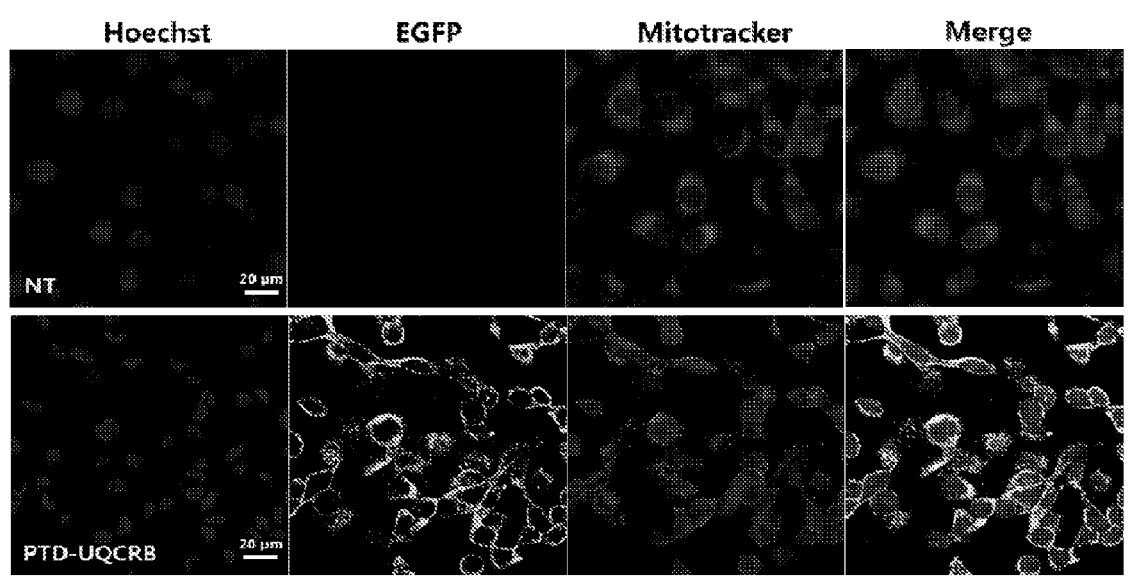

Before treatment of PTD-UQCRB fusion protein to assess its cellular functions, the ability of the protein to move into the cells was tested. To determine the localization of PTD-UQCRB fusion protein in the cells, confocal microscopy analysis was performed. Transmembrane ability of PTD-UQCRB fusion protein was detected in HT1080 cells using EGFP, co-stained with Hoechst and Mitotracker, the mitochondria detector. As shown in the image (FIG. 4), green fluorescence was detected in the samples with the treatment of PTD-UQCRB fusion protein in relevant to the control in 1 h. Hence, this result implies that PTD-UQCRB fusion protein can be delivered into the cells.

Surprisingly, green fluorescence was detected mainly in cytoplasm in comparison to nucleus. Hph1 PTD is originally known to guide its fusion partner across all cellular membranes including blood-brain barrier (BBB). This phenomenon, however, might be due to the characteristic of UQCRB. As mentioned previously, UQCRB is a nuclear-encoded component of mitochondrial Complex III[2]. This means UQCRB might have the mitochondria-targeting sequences and prediction of theses sequences with the MitoProt II±1.0a4 software suggest that 1-35 amino acids, out of 111 total amino acids composing UQCRB, undertake the mitochondria targeting signals. In this respect, PTD-UQCRB fusion protein is targeting towards the mitochondria and co-staining of mitochondria with Mitotracker validates this possibility.

3. Effect of PTD-UQCRB Fusion Protein on Cell Growth

Figure 5:
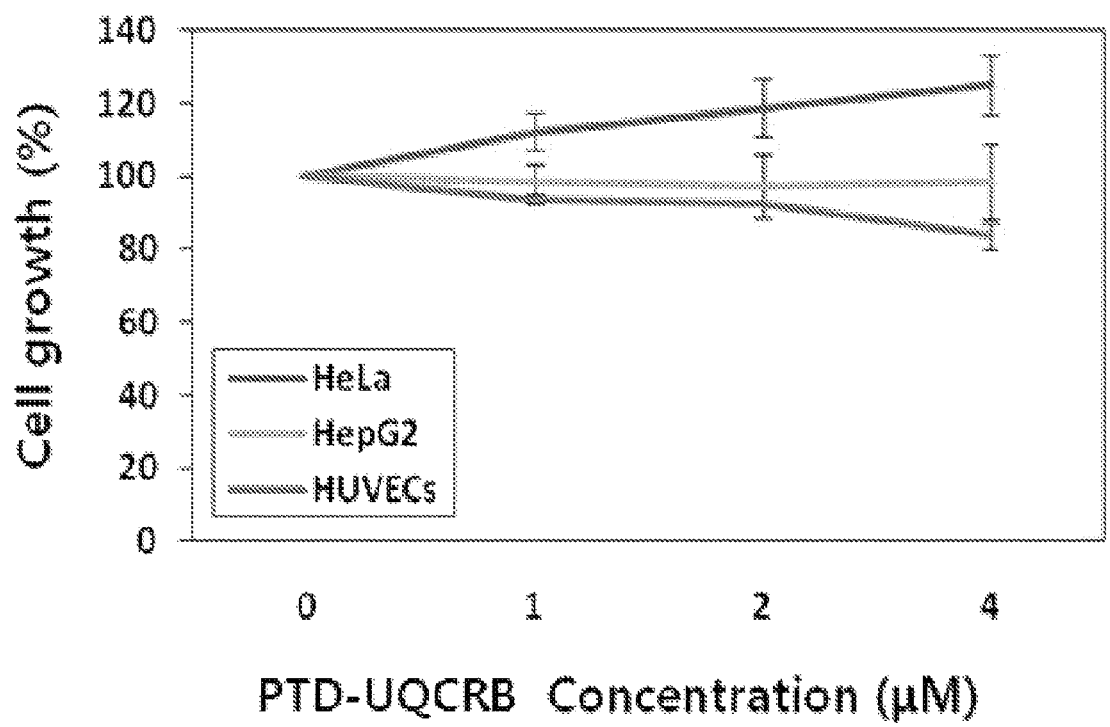
FIG. 5 represents biological activity of PTD-UQCRB on cell growth. Cell growth was measured in HeLa cells, HepG2 cells and HUVECs using MTT colorimetric assay. Data represent mean±SD from three independent experiments.

To investigate the cellular activities of PTD-UQCRB fusion protein, it is important to check the effect of the protein on cell growth because if this fusion protein is toxic for cell, the following results may not be detectable. In order to examine the bioactivity of PTD-UQCRB fusion protein on cell growth, MTT colorimetric assay was carried out in various mammalian cell lines. Three different concentrations of PTD-UQCRB fusion protein were treated to the cells and incubated for 2 days and performed MTT assay (FIG. 5). As a result, PTD-UQCRB transduction showed no significant effects on cell growth.

Figure 6A:
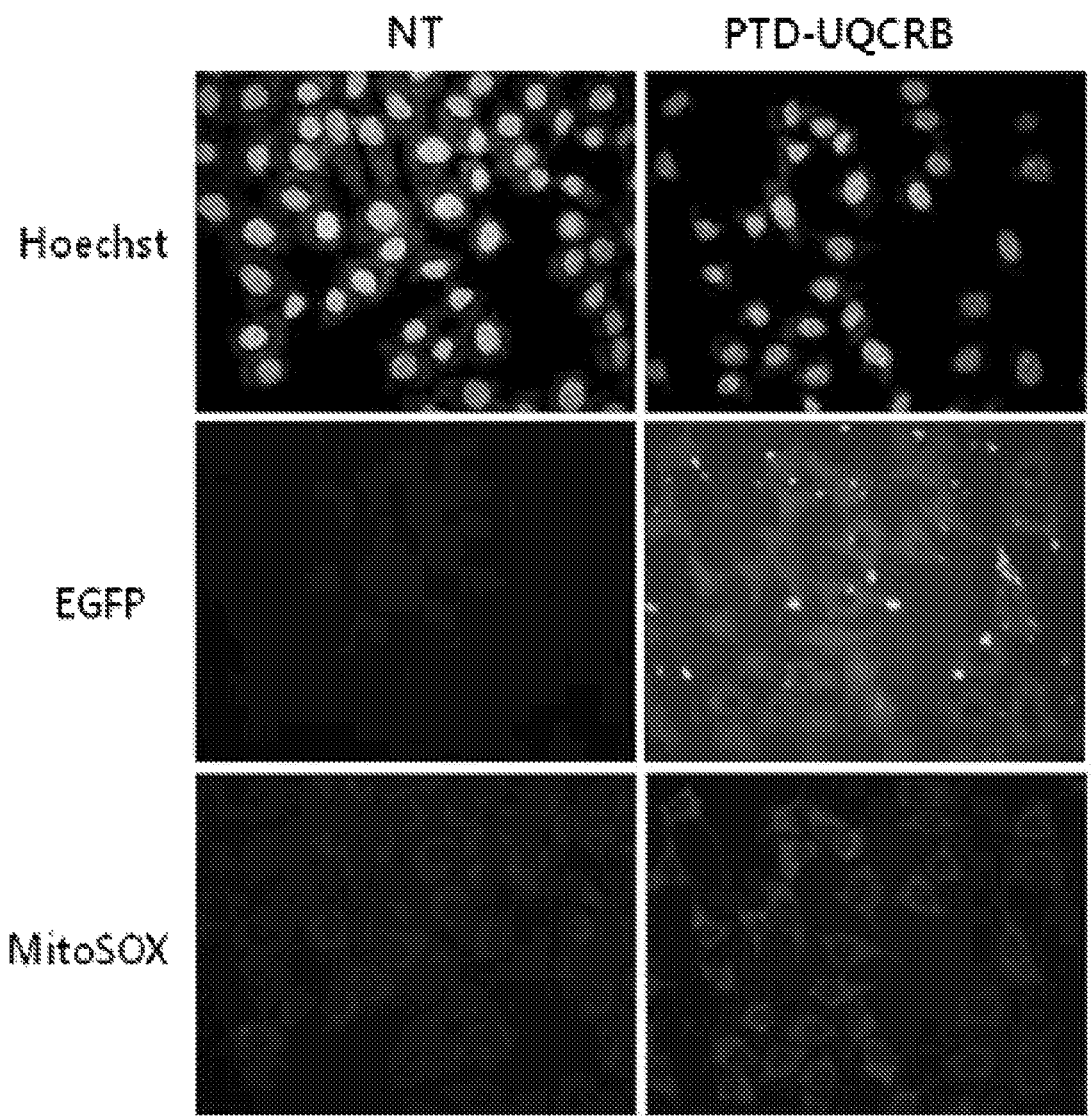
FIG. 6 represents effect of PTD-UQCRB on mitochondrial ROS generation. Mitochondrial ROS level was determined by the MitoSOX™ fluorescence in HeLa cells treated with PTD-UQCRB or antimycin A for 2 h after pre-treatment of Mito-SOX™ for 20 min. After 2 h incubation, cells were fixed and stained with Hoechst. Taken images were quantified with HCS system software. (A) Left: Fluorescent images for detection of mitochondrial ROS after treatment of 4 µM of PTD-UQCRB (NT: non-treated), Right: Bar graphs for average intensity of one cell. (B) Quantification of taken image by HCS system. Blue circle: nucleus, Green circle: cytoplasm (HCS system software recognize nucleus of a cell and set the fixed area from the nucleus to determine cytoplasm). (C) 10 µg/mL antimycin A was treated to the HeLa cells as a positive control (NT: non-treated, Ant: antimycin A). Bar graphs represent the total intensity of fluorescence. Data represent mean±SD from three independent experiments.
Figure 6C:
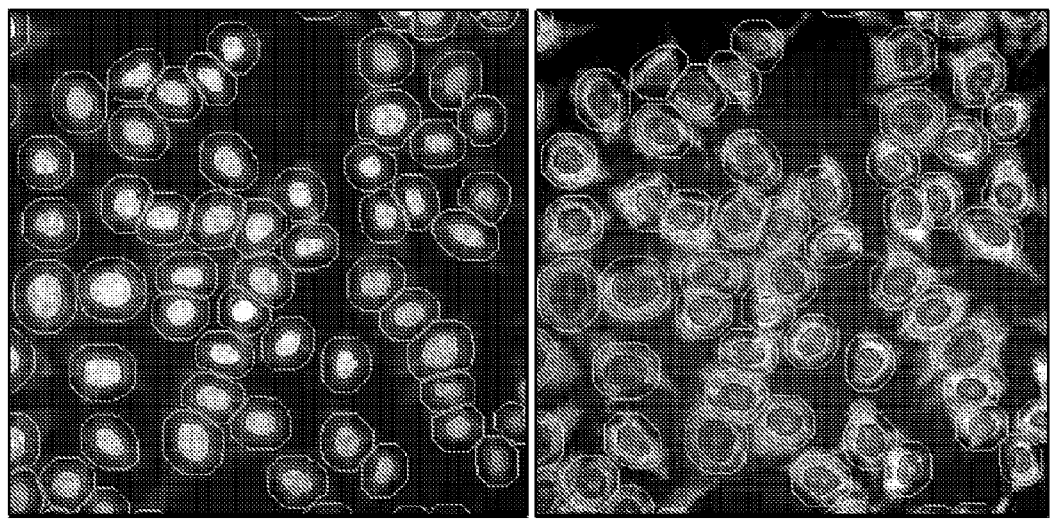
Figure 6D:
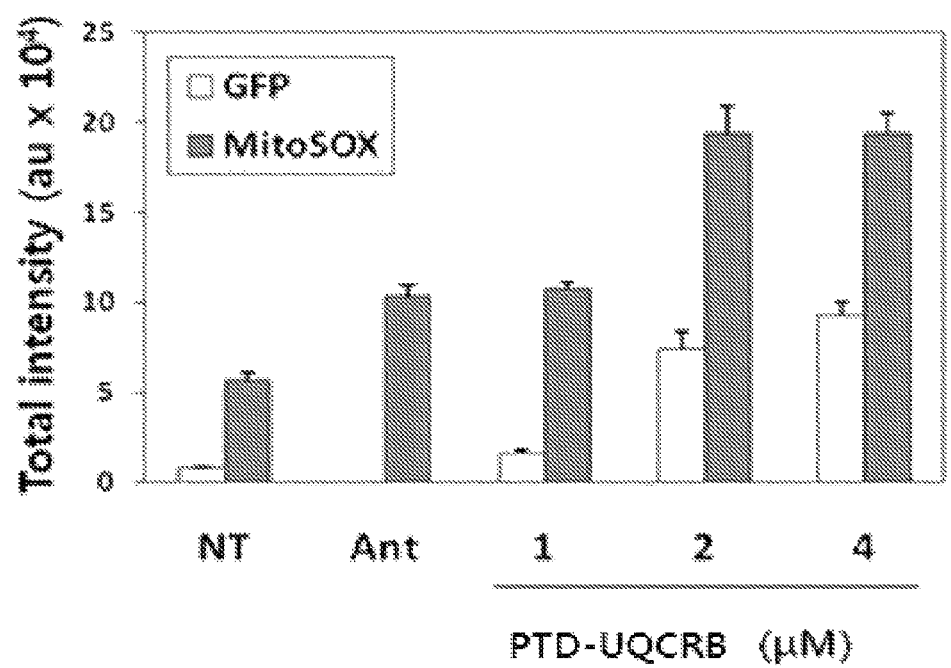

4. PTD-UQCRB Fusion Protein Enhances Mitochondrial ROS Generation and HIF-1α Stability in Normoxic Conditions Terpestacin, a small molecule which targets UQCRB, is known to inhibit mitochondrial ROS generation and HIF-1α stabilization under hypoxic conditions (Jung et al. manuscript in submission). Cellular ROS generation during hypoxia is primarily due to the Complex III of mitochondrial respiratory chains. Since UQCRB is not only a target of terpestacin but also a subunit of the Complex III of mitochondrial respiratory chains, PTD-UQCRB transduction could be assumed that it might affect ROS generation and HIF-1α stability. To examine whether PTD-UQCRB alters Complex III-derived ROS generation, mitochondrial ROS level of HeLa cells was determined using red mitochondrial superoxide indicator, MitoSOX™. Once in the mitochondria, MitoSOX™ reagent can be oxidized by mitochondrial superoxide and exhibit the red fluorescence. Intracellular delivery of PTD-UQCRB could be confirmed with green fluorescence by virtue of tagged EGFP (FIG. 6A). PTD-UQCRB transduction triggered the increase of mitochondrial ROS level as shown by the increased red fluorescence. In addition, increment of mitochondrial ROS level was detected as the concentration of PTD-UQCRB increased (FIG. 6B). Also, antimycin A, a small molecule which induces oxidative stress, augments the cellular ROS level in compare with control.

5. Effect of PTD-UQCRB on HIF-1α Stability

Figure 7A:
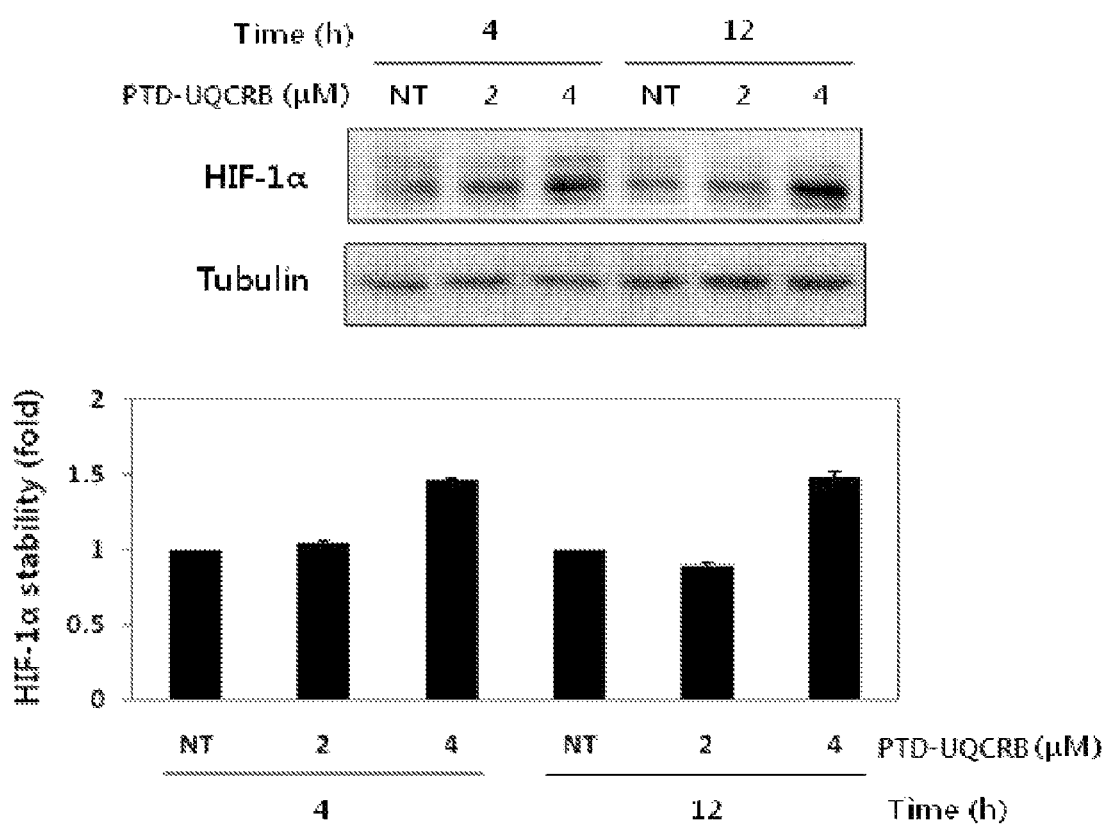
FIG. 7 represents effect of PTD-UQCRB on HIF-1α stability. (A) HIF-1α protein levels were analyzed using western blot analysis in HeLa cells treated with PTD-UQCRB (2, 4 µM) for 4 h or 12 h (NT: non-treated). Lower panel represents the quantitative data for the western blot analysis using densitometry. Data represent mean±SD from three independent experiments. (B) HIF-1α protein levels were examined using western blot analysis in HeLa cells treated with PTD-UQCRB (2, 4 µM) and PTD-EGFP (2, 4 µM) as control for 24 h (NT: non-treated). Lower panel represents the quantitative data of the western blot analysis using densitometry. Data represent mean±SD from three independent experiments.

The effects of PTD-UQCRB on HIF-1α stability in HeLa cells were investigated because the increased intracellular ROS stabilize HIF-1α protein and mediate hypoxia-induced transcription such as VEGF expression. Also, several studies demonstrated that the hypoxia-induced production of ROS in mitochondria is both necessary and sufficient for hypoxia-dependent HIF-1α accumulation[6,24-28]. Naturally, HIF-1α protein is degraded in normoxic conditions, but accumulation of HIF-1α a protein was dose dependently induced by transduction of PTD-UQCRB in HeLa cells for 4 hrs (FIG. 7A). However, 12 h after PTD-UQCRB treatment, HIF-1α protein seemed to be less induced in comparison to 4 hrs.

Figure 7B:
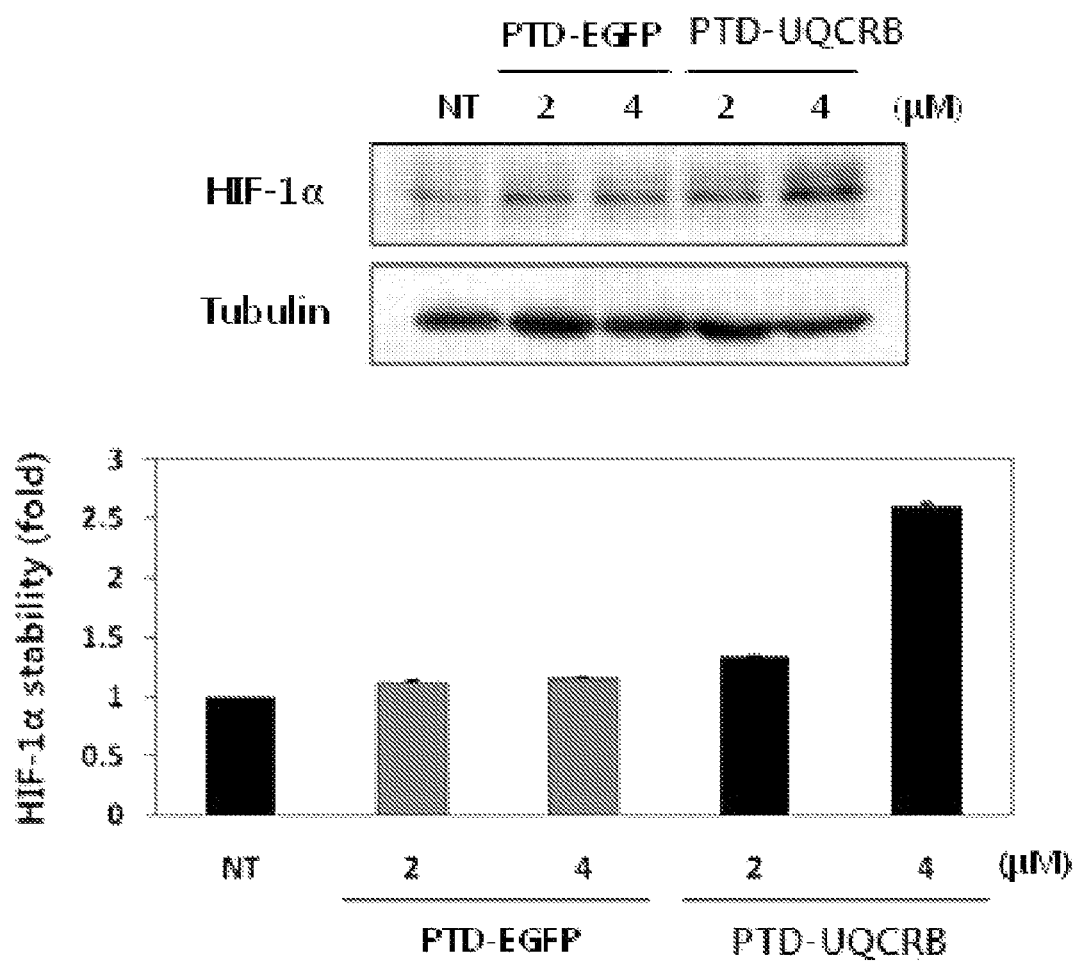

In order to validate the novel bioactivity of PTD-UQCRB on HIF-1α stability, PTD-EGFP which lacks UQCRB was utilized as control (FIG. 7B). As expected, PTD-EGFP showed no significant activities on HIF-1α stability while PTD-UQCRB stabilized HIF-1α protein remarkably.

Figure 8:
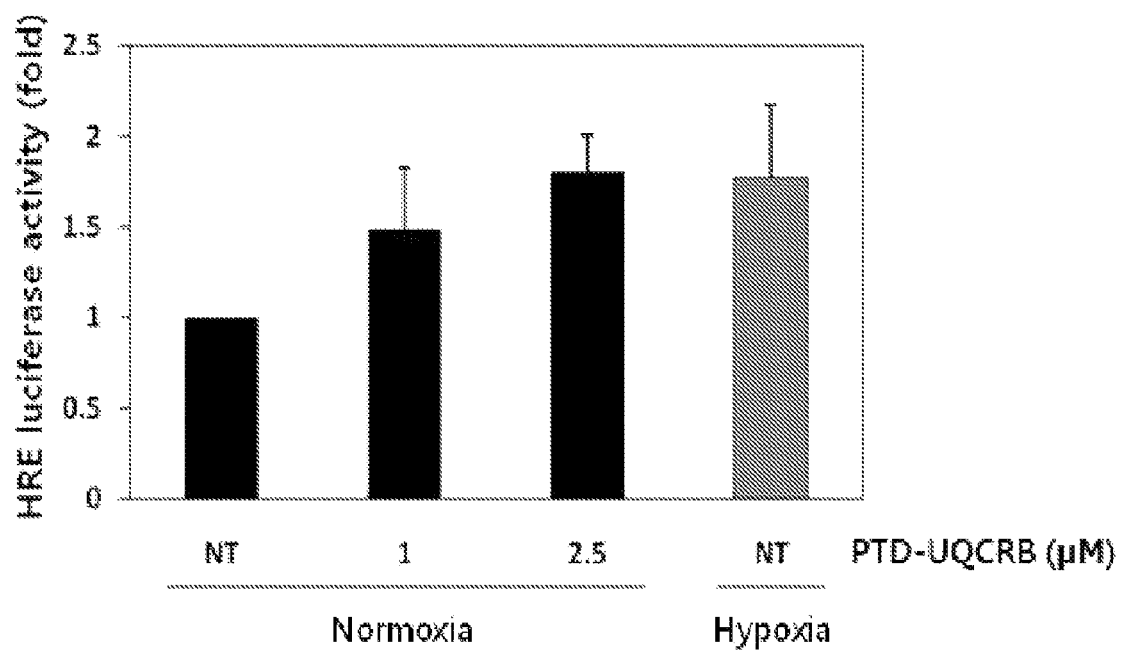
FIG. 8 represents quantitative analysis of activation of HRE reporter gene expression by PTD-UQCRB. HepG2 cells were transiently transfected with HRE-luciferase DNA vectors. Cells were treated with PTD-UQCRB (1, 2.5 µM) for 4 h (NT: non-treated). Luciferase luminescence was examined to compare the biological activities. Data represent mean±SD from three independent experiments.

Since HIF-1 activation is a multistep process, binding of HIF-1 complexes to the HIF-1 responsive promoters should be inspected along with the HIF-1α protein stability. To examine this, hypoxia-responsive element (HRE) reporter gene assay was executed in HepG2 cells (FIG. 8). PTD-UQCRB transduction to the cells transiently transfected with HRE-luciferase DNA vectors showed as much activities as hypoxia conditions did. This result implies that stabilized HIF-1α in normoxic conditions by virtue of mitochondrial ROS could dimerize with HIF-1β, translocate to the nucleus and bind to the HIF-1 responsive promoters, and form the active transcriptional complexes to express downstream gene such as VEGF.

6. PTD-UQCRB Fusion Protein Induces VEGF Expression Under Normoxia

Figure 9A:
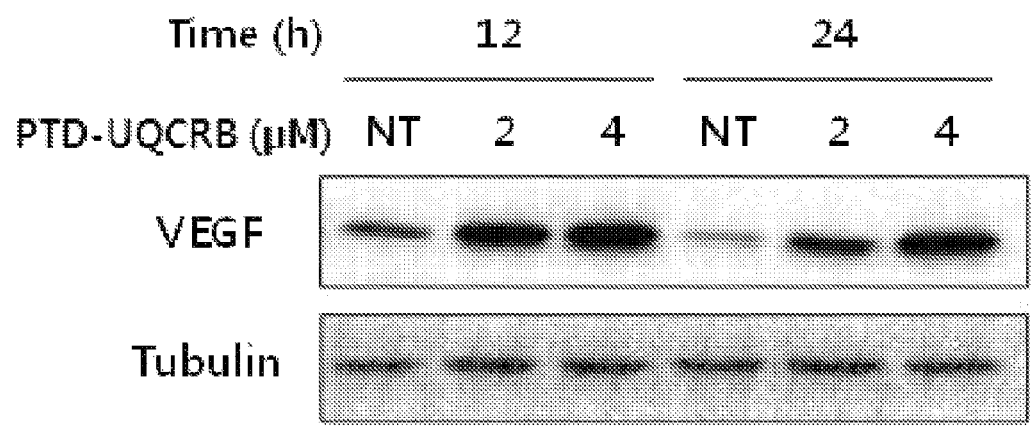
FIG. 9 represents effect of PTD-UQCRB on VEGF expression. VEGF protein levels were analyzed using western blot analysis in cells treated with PTD-UQCRB (2, 4 µM) for 12 or 24 h (NT: non-treated). (A) VEGF induction in HeLa cells. (B) VEGF induction in HepG2 cells. (C) Bar graphs represent the quantitative data of the western blot analysis using densitometry. Data represent mean±SD from three independent experiments. (D) VEGF protein levels were examined using western blot analysis in HeLa cells treated with PTD-UQCRB (2, 4 µM) and PTD-EGFP (2, 4 µM) as control for 24 h (NT: non-treated). Lower panel represents the quantitative results of the western blot analysis using densitometry. Data represent mean±SD from three independent experiments. (E) Angiogenic effect of PTD-UQCRB in HUVECs. HeLa cells were treated with PTD-UQCRB (2, 4 µM) for 12 h and 24 h in all free medium before collecting CM (NT: non-treated). HUVECs was incubated for 16 h in the CM and cell morphology was photographed. The collected CM stimulates the invasiveness of HUVECs. Control and VEGF were used as positive control. (F) Densitometrical analysis of invasion assay. Data represent mean±SD from three independent experiments.
Figure 9B:
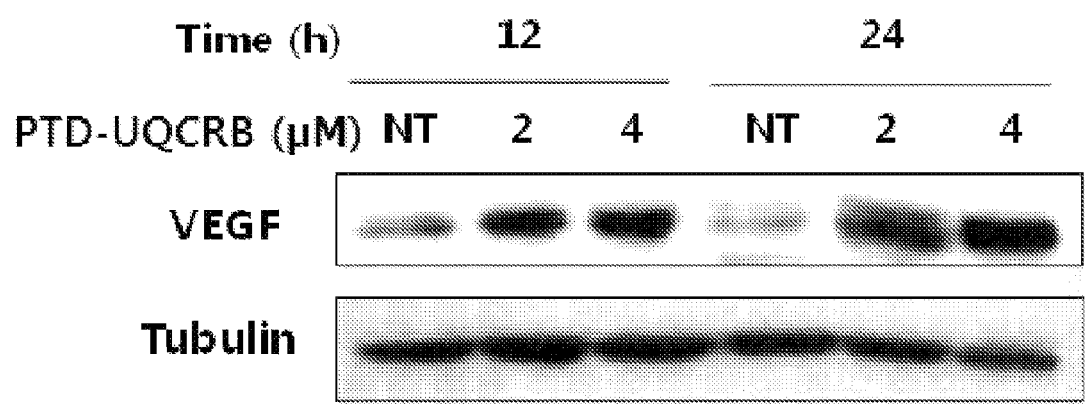
Figure 9C:
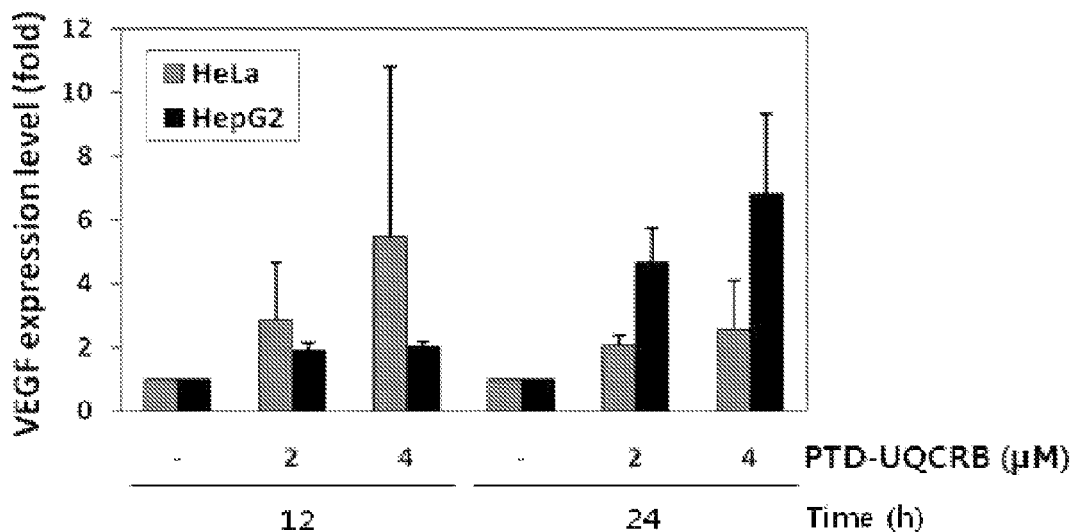

As mentioned before, the stability of HIF-1α is a crucial regulatory step for the transcription of HIF-1α target genes. VEGF is a major target gene of HIF-1α and carries out an important role in hypoxia-induced angiogenesis. Hence, the effect of PTD-UQCRB on VEGF expression was analyzed in HeLa cells (FIG. 9A) and HepG2 cells (FIG. 9B). As compared to control, intracellular delivery of PTD-UQCRB dose-dependently increased VEGF protein level in both cell lines (FIG. 9C).

Figure 9D:
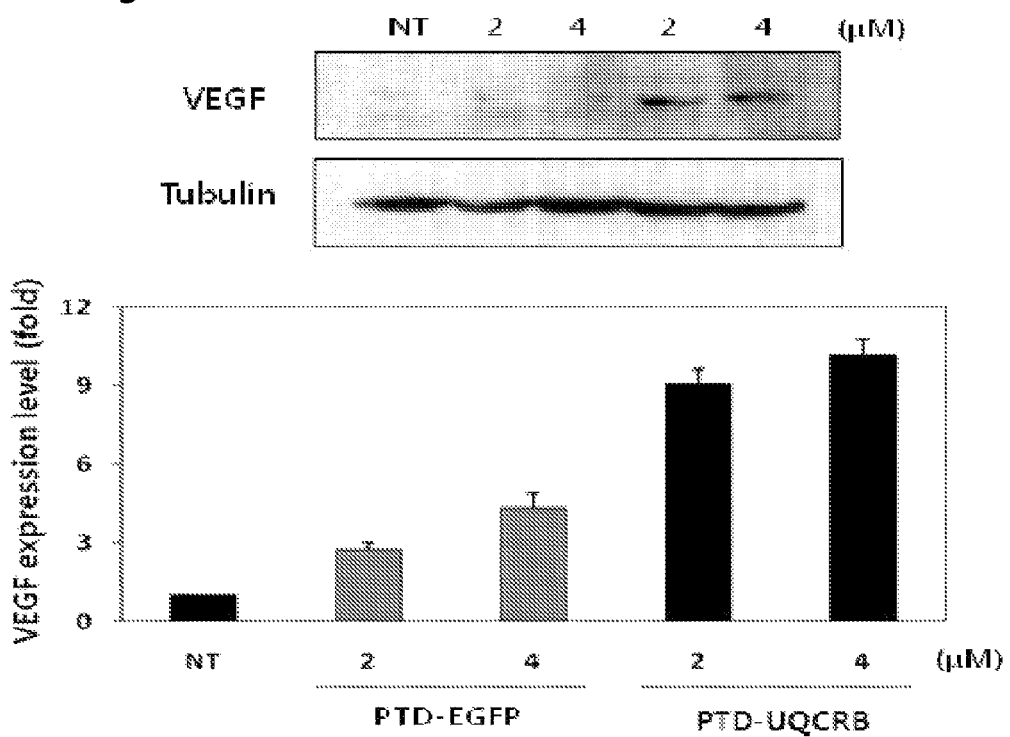

So as to confirm the novel bioactivity of PTD-UQCRB on VEGF induction, PTD-EGFP which lacks UQCRB was used as control (FIG. 9D). Subsequently, PTD-EGFP showed no significant activities on VEGF expression whereas PTD-UQCRB profoundly induced VEGF.

Figure 9E:
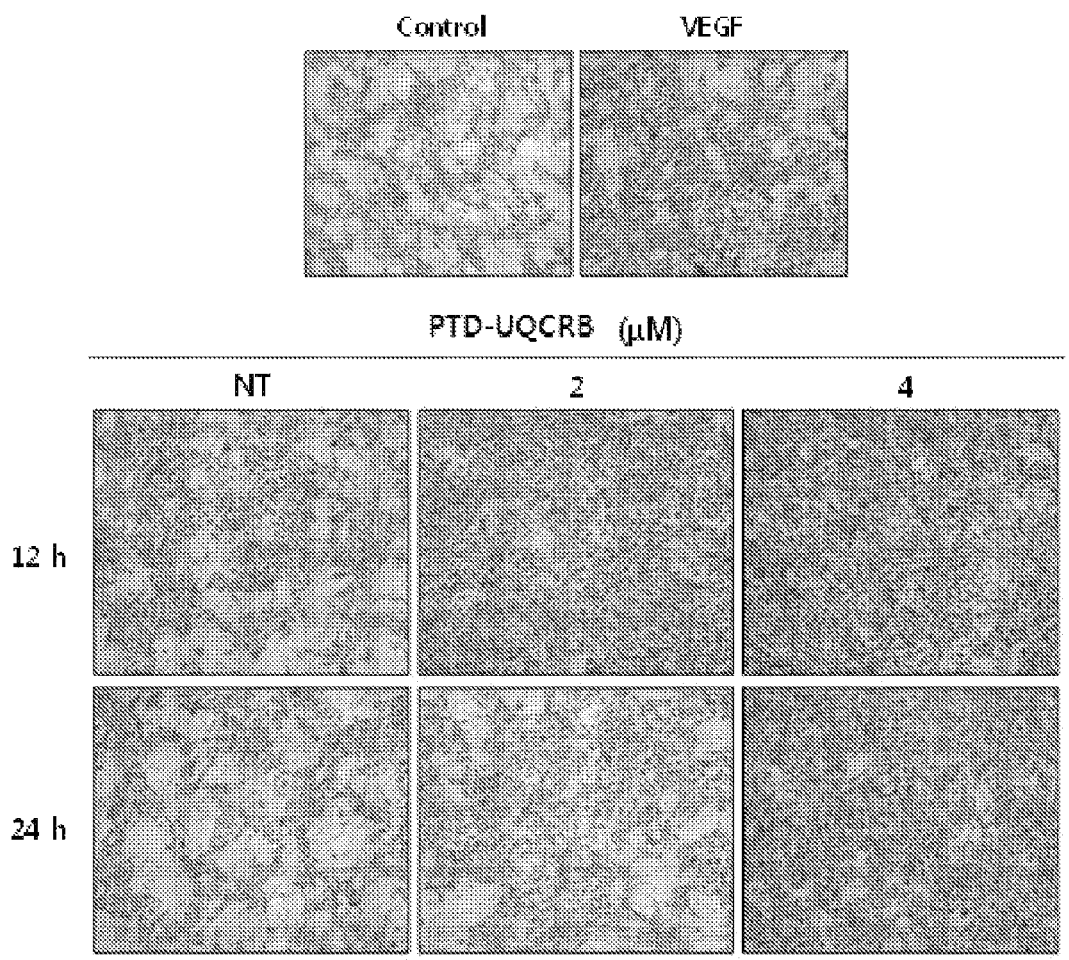
Figure 9F:
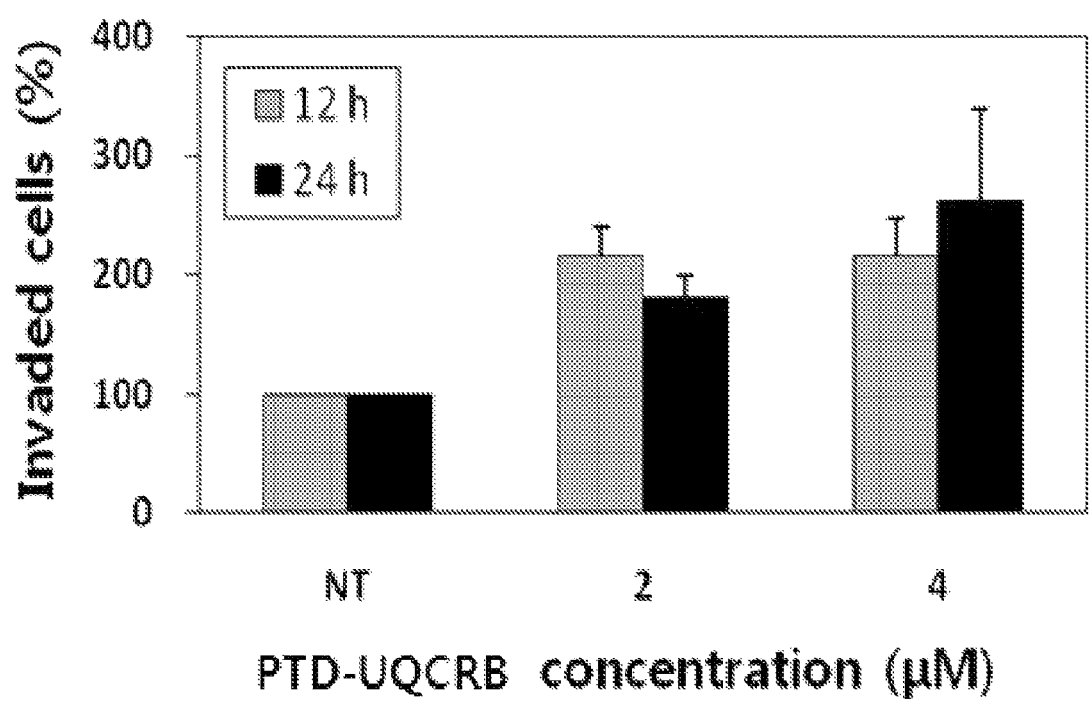

Next, in order to investigate the angiogenic activity of PTD-UQCRB, the conditioned medium (CM) from HeLa cells incubated in each culture condition were collected and subjected to in vitro angiogenesis assay (FIG. 9E). The CM was in all free medium, concentrated by filtration and finally prepared in distilled water. The CM from HeLa cells incubated with PTD-UQCRB strongly activated the invasion of HUVECs. These results are well consistent with the on-going study of UQCRB by our lab about UQCRB gene overexpression. In this respect, these data clearly demonstrate that PTD-UQCRB is an effective tool for exploring the biological function of UQCRB.

7. PTD-UQCRB Fusion Protein Affects in Vivo Wound Healing

Figure 10A:
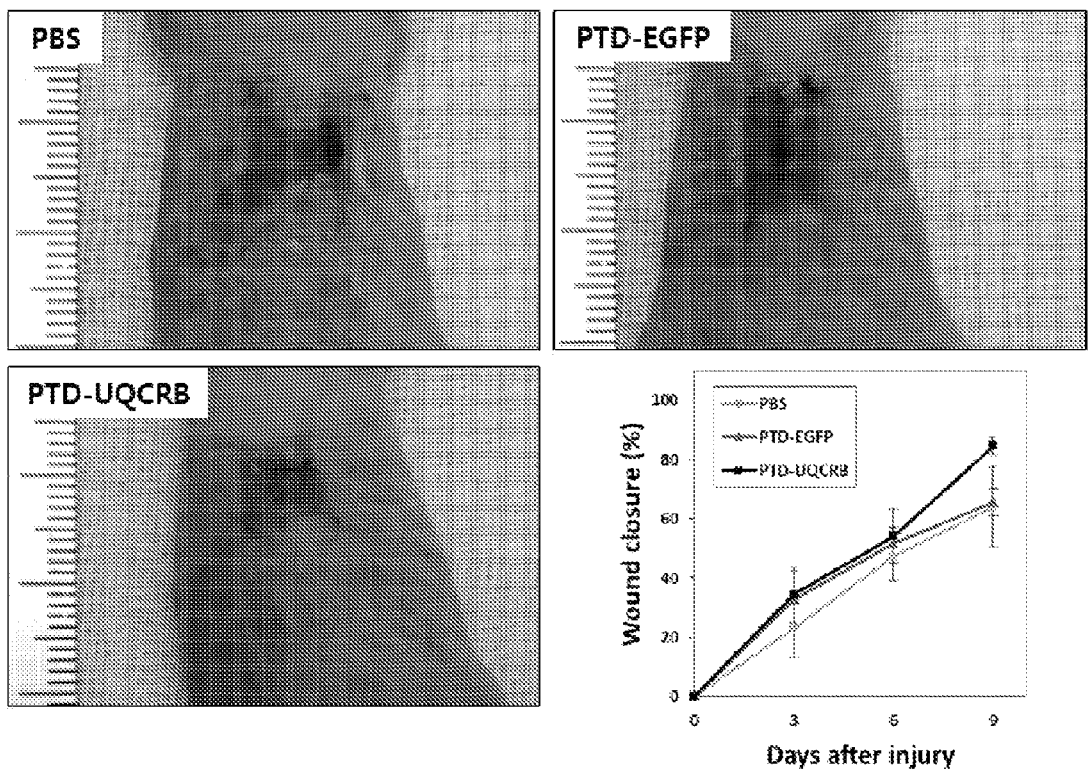
FIG. 10 represents effect of PTD-UQCRB on wound healing in vivo. BALB/c nude (n=7) mice were divided into three (3) groups, PTD-UQCRB, PTD-EGFP and PBS to verify effect of PTD-UQCRB on wound healing. (A) Images on 9 days after surgery and quantitative analysis results of wound size on 3 days after surgery. (B) Results of histological or immunohistochemical staining on 14 days after surgery (H-E: hematoxylin-eosin, M-T: Masson's trichrome, SMA: smooth muscle α-actin). Arrows in each image indicate the epidermal thickness (H-E, M-T and involucrin) or the arteriole (SMA). (C) Quantitative analysis of regenerated epidermal thickness. (D) Quantitative analysis for the number of arteriole in wound healing portion.

Based on effective angiogenesis activity verified inside the cell, in order to validate the action of PTD-UQCRB fusion protein, the wound healing model which is mainly used for verifying angiogenesis effect was applied to experiment. 5-week-old BALB/c nude mouse was wounded in its back and treated with mixtures of PTD-UQCRB fusion protein and the fibrin matrix to cure the back injury. Velocity of wound healing in PTD-EGFP as negative control of PTD-UQCRB, and PBS-treated group show relatively slow as compared to PTD-UQCRB-treated group (FIG. 10A). In addition, it showed very effective wound healing activity on 6-9 days after surgical treatment of PTD-UQCRB.

Figure 10B:
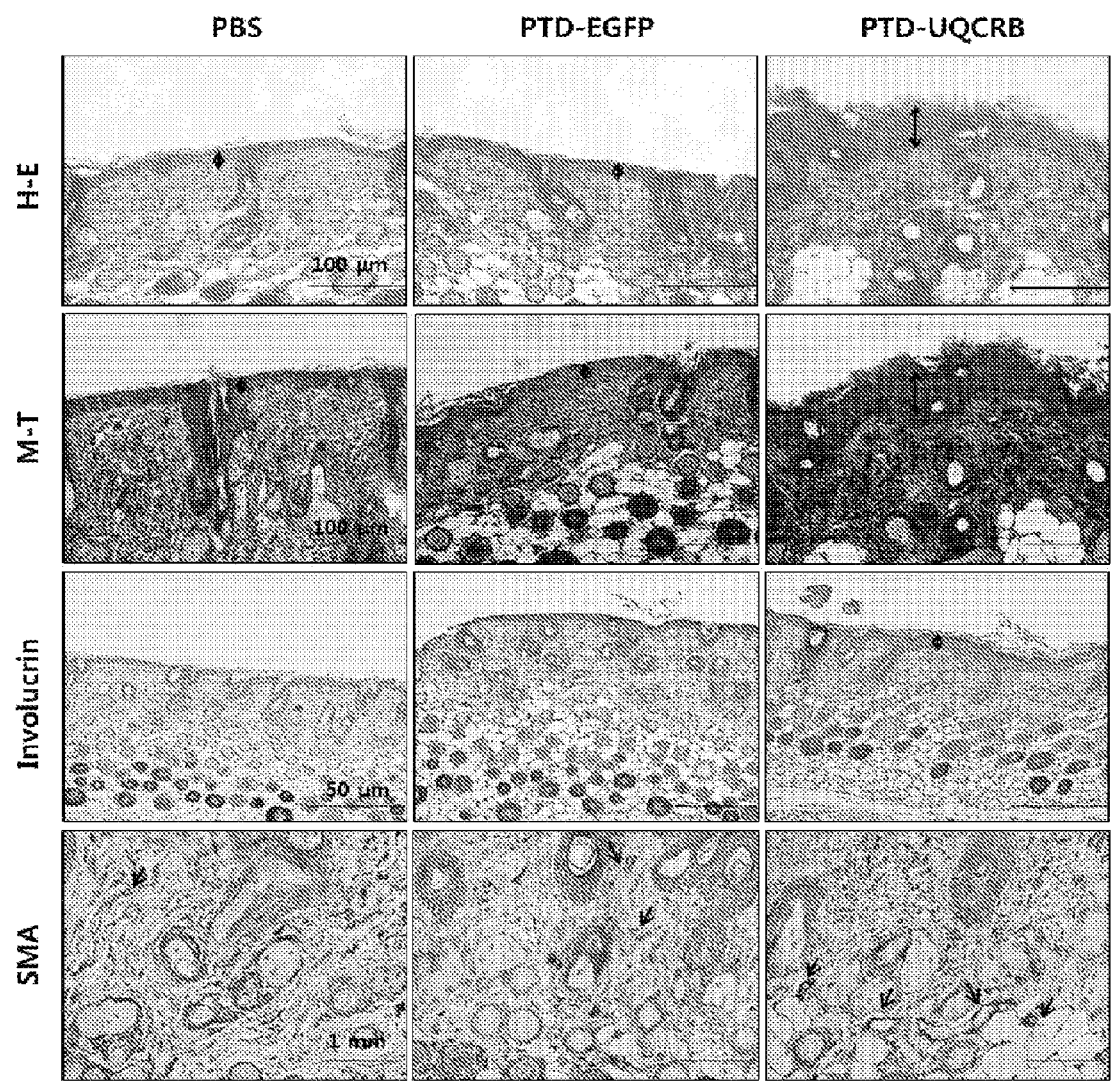
Figure 10C:
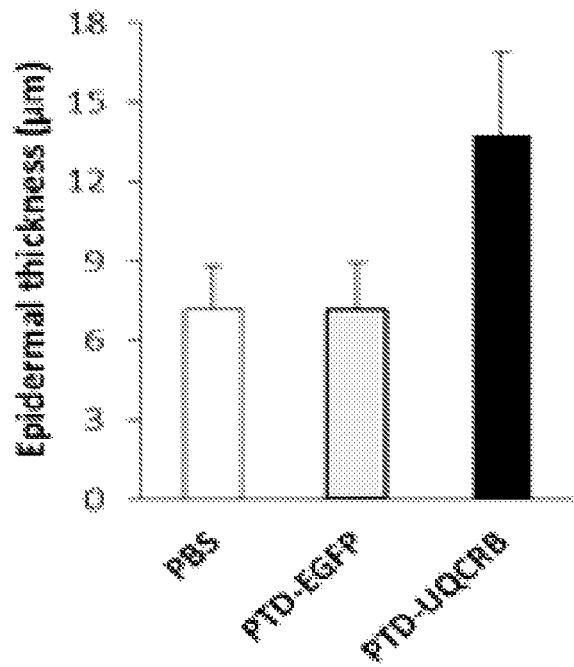
Figure 10D:
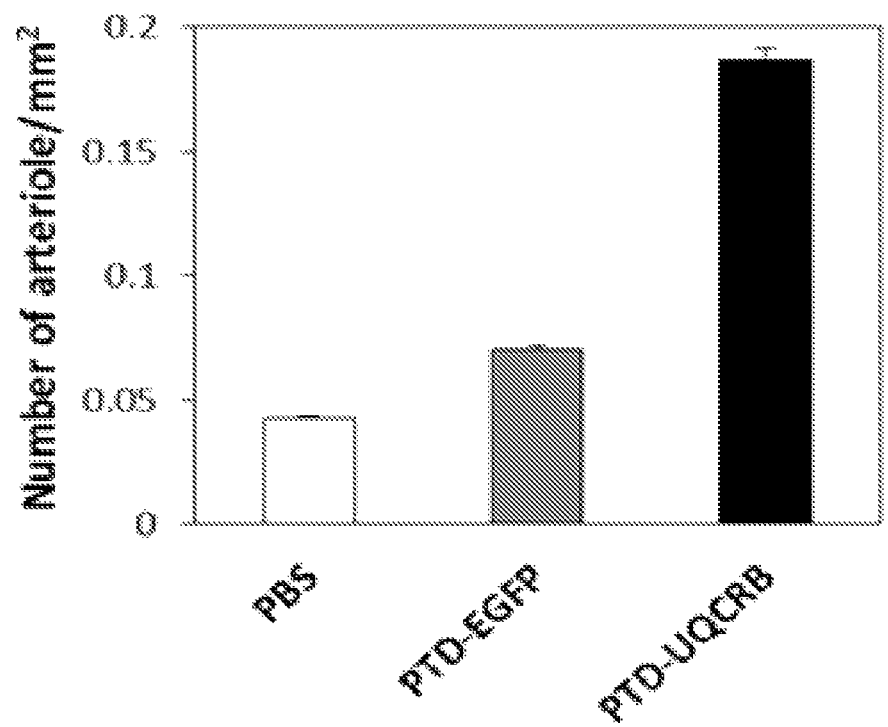
Figure 11:
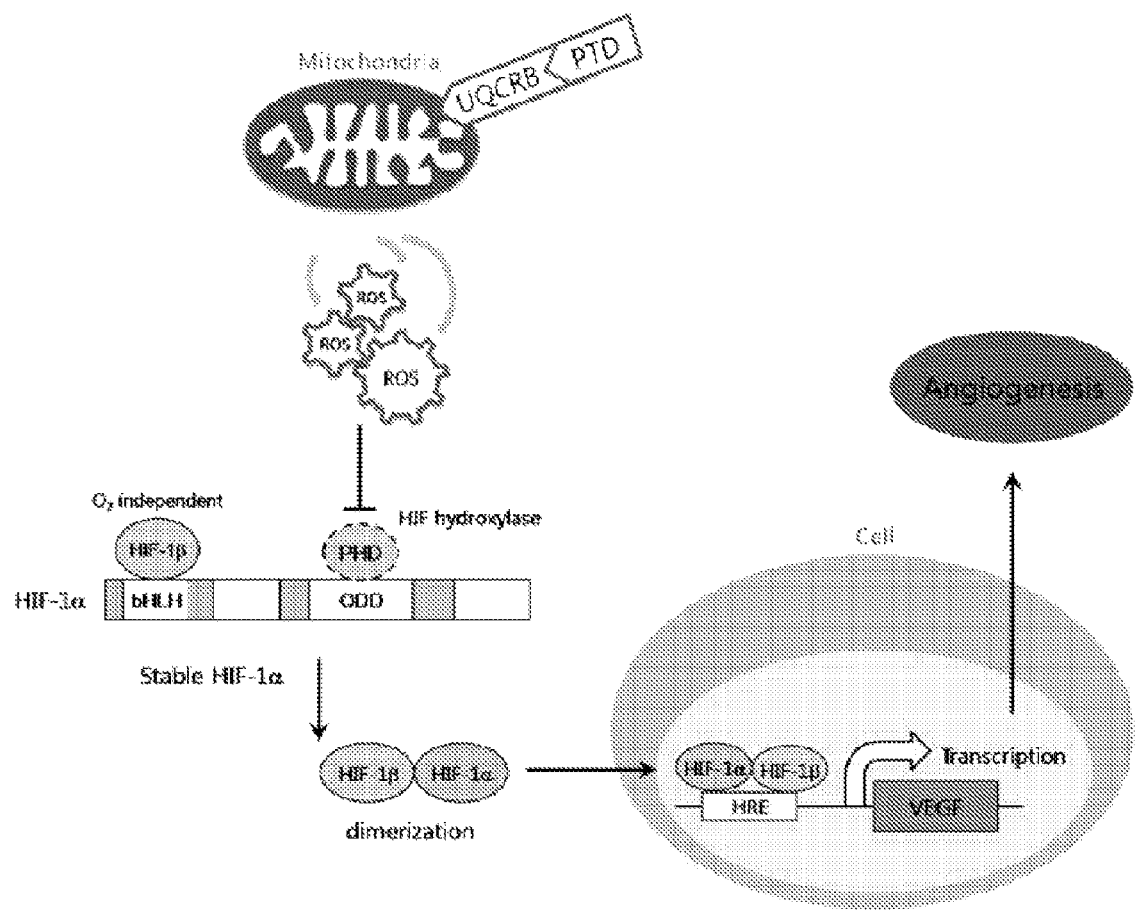
FIG. 11 represents schematic diagram of PTD-UQCRB function. When PTD-UQCRB fusion protein permeates into the cells, the mitochondrial Complex III-derived ROS generation is induced. Mitochondrial ROS inhibits PHD, the HIF hydroxylase, to stabilize HIF-1α. Stable HIF-1α can dimerize with HIF-1β and the heterodimer complex translocates into the nucleus to bind on HRE promoter. Consequently, the target gene such as VEGF can be transcribed and lead to angiogenesis.

Mouse was euthanized on 14 days after surgery and histological or immunohistochemical (IHC) analysis was performed (FIG. 10B). The epidermal thickness in a regenerated portion may be measured by H-E, M-T staining and involucrin antibody-using staining The epidermal thickness in the PTD-UQCRB-treated group was observed to be approximately two-fold thicker than that in the PTD-EGFP-treated or PBS-treated group (FIG. 10C). In addition, the immunohistochemical staining results using SMA showed that the PTD-UQCRB-treated group was generated more arterioles than other groups. It was quantitatively analyzed that the PTD-UQCRB-treated group were generated 3-4 fold more arterioles (per mm$^2$) than the two negative control groups, demonstrating that the PTD-UQCRB effectively promote angiogenesis in vivo (FIG. 10D). These results suggest that the treatment of the PTD-UQCRB exhibits effectiveness in angiogenesis and wound healing in vivo animal model, addressing that the PTD-UQCRB is a promising angiogenesis induction agent.

Discussion

In the present study, the novel PTD-UQCRB fusion protein was constructed to accomplish the intracellular delivery of UQCRB. Purified PTD-UQCRB was treated to the cells in order to investigate its intracellular activities on mitochondrial Complex III.

Since UQCRB, a target protein of anti-angiogenic agent terpestacin, is a component of mitochondrial Complex III, transduction of PTD-UQCRB has been expected to induce angiogenesis. Indeed, treatment of PTD-UQCRB induces the generation of mitochondrial superoxide and enhances HIF-1α stability as well. Moreover, PTD-UQCRB transduction induces VEGF expression and invasion of HUVECs in vitro. As inferred from the results of the cellular activities of PTD-UQCRB, it appears to play a key role in mitochondrial function leads to angiogenesis (FIG. 10). This finding can be expanded to the clinical applications for wound healing or limb formation in a diabetic mouse model via enhanced angiogenesis.

Further studies for validation of PTD-UQCRB activities will strengthen the discovery of this study. First, it would be better to investigate the biological activities of PTD-UQCRB on normal cell lines. As described above, we used tumor cell lines in vitro assays to have better sensitivity upon PTD-UQCRB treatment. Considering pro-angiogenic activity of PTD-UQCRB, it is necessary to evaluate the effect of PTD-UQCRB on normal cells such as HUVECs or CHANG (normal liver cells), whether they can exhibit the same activity or not. For this reason, examining the pro-angiogenic activity of PTD-UQCRB on HUVECs is on-going. Second, generation of various DNA constructs to encode PTD-UQCRB without EGFP, UQCRB alone and mutant form of UQCRB fused with PTD will validate the novel function of PTD-UQCRB. To produce these DNA constructs, gene cloning is under the procedure. Next, detection of changes in HIF-1α stability and VEGF expression level after treatment of PTD-UQCRB on cells with terpestacin will confirm the specific bioactivity of PTD-UQCRB.

In conclusion, all the outcomes in this study suggest that PTD-UQCRB could be a meaningful means to examine the cellular activities of UQCRB. In addition, these results will provide new insights into the function of PTD-UQCRB on mitochondria mediated ROS generation which is linked to angiogenesis and also open new basis on adaptation of PTD for developing biologically active proteins.

Having described an embodiment of the present invention, it is to be understood that variants and modifications thereof falling within the spirit of the invention may become apparent to those skilled in this art, and the scope of this invention is to be determined by appended claims and their equivalents.

REFERENCE

1. Jung, H. J., Lee, H. B., Kim, C. J., Rho, J. R., Shin, J. & Kwon, H. J. Anti-angiogenic activity of terpestacin, a bicyclo sesterterpene from Embellisia chlamydospora. J Antibiot (Tokyo) 56, 492-496 (2003).
2. Suzuki, H., Hosokawa, Y., Toda, H., Nishikimi, M. & Ozawa, T. Cloning and sequencing of a cDNA for human mitochondrial ubiquinone-binding protein of complex III. Biochem Biophys Res Commun 156, 987-994 (1988).
3. Hemrika, W., De Jong, M., Berden, J. A. & Grivell, L. A. The C-terminus of the 14-kDa subunit of ubiquinol-cytochrome-c oxidoreductase of the yeast Saccharomyces cerevisiae is involved in the assembly of a functional enzyme. Eur J Biochem 220, 569-576 (1994).
4. Haut, S., Brivet, M., Touati, G., Rustin, P., Lebon, S., Garcia-Cazorla, A., Saudubray, J. M., Boutron, A., Legrand, A. & Slama, A. A deletion in the human QP-C gene causes a complex III deficiency resulting in hypoglycaemia and lactic acidosis. Hum Genet 113, 118-122 (2003).
5. Guzy, R. D. & Schumacker, P. T. Oxygen sensing by mitochondria at complex III: the paradox of increased reactive oxygen species during hypoxia. Exp Physiol 91, 807-819 (2006).
6. Guzy, R. D., Hoyos, B., Robin, E., Chen, H., Liu, L., Mansfield, K. D., Simon, M. C., Hammerling, U. & Schumacker, P. T. Mitochondrial complex III is required for hypoxia-induced ROS production and cellular oxygen sensing. Cell Metab 1, 401-408 (2005).
7. Drose, S. & Brandt, U. The mechanism of mitochondrial superoxide production by the cytochrome bc1 complex. J Biol Chem 283, 21649-21654 (2008).
8. Schumacker, P. T. Current paradigms in cellular oxygen sensing. Adv Exp Med Biol 543, 57-71 (2003).
9. Chandel, N. S., McClintock, D. S., Feliciano, C. E., Wood, T. M., Melendez, J. A., Rodriguez, A. M. & Schumacker, P. T. Reactive oxygen species generated at mitochondrial complex III stabilize hypoxia-inducible factor-1alpha during hypoxia: a mechanism of O2 sensing. J Biol Chem 275, 25130-25138 (2000).
10. Semenza, G. L. HIF-1: mediator of physiological and pathophysiological responses to hypoxia. J Appl Physiol 88, 1474-1480 (2000).
11. Iyer, N. V., Kotch, L. E., Agani, F., Leung, S. W., Laughner, E., Wenger, R. H., Gassmann, M., Gearhart, J. D., Lawler, A. M., Yu, A. Y. & Semenza, G. L. Cellular and developmental control of O2 homeostasis by hypoxia-inducible factor 1 alpha. Genes Dev 12, 149-162 (1998).
12. Wang, G. L., Jiang, B. H., Rue, E. A. & Semenza, G. L. Hypoxia-inducible factor 1 is a basic-helix-loop-helix-PAS heterodimer regulated by cellular O2 tension. Proc Natl Acad Sci USA 92, 5510-5514 (1995).
13. Forsythe, J. A., Jiang, B. H., Iyer, N. V., Agani, F., Leung, S. W., Koos, R. D. & Semenza, G. L. Activation of vascular endothelial growth factor gene transcription by hypoxia-inducible factor 1. Mol Cell Biol 16, 4604-4613 (1996).
14. Hirota, K. & Semenza, G. L. Regulation of angiogenesis by hypoxia-inducible factor 1. Crit Rev Oncol Hematol 59, 15-26 (2006).
15. Jung, H. J., Shim, J. S., Lee, J., Song, Y. M., Park, K. C., Choi, S. H., Kim, N. D., Yoon, J. H., Mungai, P. T., Schumacker, P. T., Kwon, H. J. Terpestacin inhibits tumor angiogenesis by targeting UQCRB of mitochondrial complex III and suppressing hypoxia-induced reactive oxygen species production and cellular oxygen sensing. J Biol Chem 285, 11584-11595 (2010).
16. Heitz, F., Morris, M. C. & Divita, G. Twenty years of cell-penetrating peptides: from molecular mechanisms to therapeutics. Br J Pharmacol 157, 195-206 (2009).
17. Schwarze, S. R. & Dowdy, S. F. In vivo protein transduction: intracellular delivery of biologically active proteins, compounds and DNA. Trends Pharmacol Sci 21, 45-48 (2000).
18. Ford, K. G., Souberbielle, B. E., Darling, D. & Farzaneh, F. Protein transduction: an alternative to genetic intervention? Gene Ther 8, 1-4 (2001).
19. Prochiantz, A. Messenger proteins: homeoproteins, TAT and others. Curr Opin Cell Biol 12, 400-406 (2000).
20. Patel, L. N., Zaro, J. L. & Shen, W. C. Cell penetrating peptides: intracellular pathways and pharmaceutical perspectives. Pharm Res 24, 1977-1992 (2007).
21. Frankel, A. D. & Pabo, C. O. Cellular uptake of the tat protein from human immunodeficiency virus. Cell 55, 1189-1193 (1988).
22. Morris, M. C., Depollier, J., Mery, J., Heitz, F. & Divita, G. A peptide carrier for the delivery of biologically active proteins into mammalian cells. Nat Biotechnol 19, 1173-1176 (2001).
23. Choi, J. M., Ahn, M. H., Chae, W. J., Jung, Y. G., Park, J. C., Song, H. M., Kim, Y. E., Shin, J. A., Park, C. S., Park, J. W., Park, T. K., Lee, J. H., Seo, B. F., Kim, K. D., Kim, E. S., Lee, D. H., Lee, S. K. & Lee, S. K. Intranasal delivery of the cytoplasmic domain of CTLA-4 using a novel protein transduction domain prevents allergic inflammation. Nat Med 12, 574-579 (2006).
24. Chandel, N. S., Maltepe, E., Goldwasser, E., Mathieu, C. E., Simon, M. C. & Schumacker, P. T. Mitochondrial reactive oxygen species trigger hypoxia-induced transcription. Proc Natl Acad Sci USA 95, 11715-11720 (1998).
25. Klimova, T. & Chandel, N. S. Mitochondrial complex III regulates hypoxic activation of HIF. Cell Death Differ 15, 660-666 (2008).
26. Brunelle, J. K., Bell, E. L., Quesada, N. M., Vercauteren, K., Tiranti, V., Zeviani, M., Scarpulla, R. C. & Chandel, N. S. Oxygen sensing requires mitochondrial ROS but not oxidative phosphorylation. Cell Metab 1, 409-414 (2005).
27. Mansfield, K. D., Guzy, R. D., Pan, Y., Young, R. M., Cash, T. P., Schumacker, P. T. & Simon, M. C. Mitochondrial dysfunction resulting from loss of cytochrome c impairs cellular oxygen sensing and hypoxic HIF-alpha activation. Cell Metab 1, 393-399 (2005).
28. Lin, X., David, C. A., Donnelly, J. B., Michaelides, M., Chandel, N. S., Huang, X., Warrior, U., Weinberg, F., Tormos, K. V., Fesik, S. W. & Shen, Y. A chemical genomics screen highlights the essential role of mitochondria in HIF-1 regulation. Proc Natl Acad Sci USA 105, 174-179 (2008).

What is claimed is:

1. A PTD-UQCRB fusion polypeptide comprising the amino acid sequence of a PTD (protein transduction domain) set forth in SEQ ID NO:2 and the amino acid sequence of the human UQCRB (Ubiquinol-cytochrome c reductase binding protein) as set forth in SEQ ID NO:1.

2. A method for treating an ischemic disease, comprising administering to a subject in need thereof a pharmaceutical composition comprising (a) a pharmaceutically effective amount of a PTD-UQCRB fusion polypeptide comprising the amino acid sequence of a PTD (protein transduction domain) set forth in SEQ ID NO:2 and the amino acid sequence of the human UQCRB (Ubiquinol-cytochrome c reductase binding protein) as set forth in SEQ ID NO:1; and (b) a pharmaceutically acceptable carrier.

3. The method according to claim 2, wherein the PTD-UQCRB fusion polypeptide induces angiogenesis.

4. The method according to claim 2, wherein the ischemic disease is selected from the group consisting of ischemic heart disease, ischemic myocardial infarction, ischemic heart failure, ischemic enteritis, ischemic vascular disease, ischemic eye disease, ischemic retinopathy, ischemic glaucoma, ischemic renal failure, ischemic bald disease, ischemic stroke and ischemic limb disease.

* * * * *